United States Patent [19]

Guthikonda et al.

[11] Patent Number: 5,138,050
[45] Date of Patent: Aug. 11, 1992

[54] 6-AMIDO-1-METHYL CARBAPENEMS

[75] Inventors: Ravindra N. Guthikonda, Edison; Frank P. DiNinno, Old Bridge; Thomas N. Salzmann, Plainfield, all of N.J.

[73] Assignee: Merck & Co., Inc., Rahway, N.J.

[21] Appl. No.: 668,800

[22] Filed: Mar. 7, 1991

Related U.S. Application Data

[63] Continuation-in-part of Ser. No. 213,398, Jun. 30, 1988, abandoned, which is a continuation of Ser. No. 371,358, Jun. 26, 1989, abandoned.

[51] Int. Cl.$^5$ ..................................... C07D 205/085
[52] U.S. Cl. ..................................... 540/364; 540/302
[58] Field of Search .................. 540/302, 350, 364

[56] References Cited

U.S. PATENT DOCUMENTS

| | | | |
|---|---|---|---|
| 4,206,218 | 6/1980 | Christensen et al. | 540/350 |
| 4,217,453 | 8/1980 | Christensen et al. | 540/350 |
| 4,218,459 | 8/1980 | Cama et al. | 540/350 |
| 4,218,463 | 8/1980 | Christensen et al. | 540/350 |
| 4,260,627 | 4/1981 | Christensen et al. | 540/350 |
| 4,277,482 | 7/1981 | Christensen et al. | 540/350 |
| 4,298,741 | 11/1981 | Christensen et al. | 540/350 |
| 4,347,355 | 8/1982 | Chu | 540/350 |
| 4,348,264 | 9/1982 | Rosati | 540/350 |
| 4,407,815 | 10/1983 | Pearson et al. | 540/350 |
| 4,771,135 | 9/1988 | Blaszczak | 540/360 |

FOREIGN PATENT DOCUMENTS

| | | |
|---|---|---|
| 0045198 | 2/1982 | European Pat. Off. |
| 0073100 | 3/1983 | European Pat. Off. |
| 116854 | 8/1984 | European Pat. Off. |
| 237027 | 9/1987 | European Pat. Off. |
| 3509769 | 9/1986 | Fed. Rep. of Germany |
| 58-174382 | 10/1983 | Japan |
| 63-48274 | 3/1988 | Japan |

OTHER PUBLICATIONS

Larock, Comprehensive Organic Transformations pp. 193–196 (1989).
Shih, D. H., et al., Heterocycles, vol. 21, No. 1 1984, pp. 29–40.
Koller, W., et al., Tetrahedron Ltrs., vol. 23, No. 15, pp. 1545–1548, (1982).
Yamamoto, K., et al., Tetrahedron Ltrs., vol. 23, No. 50, pp. 5339–5342, (1982).
Branch, C. L., et al., J. Chem. Soc. Perkin Trans I, (1982), pp. 2123–2129.
Hakimelahi, G. H., Helvetica Chimica Agta, vol. 65, Fasc. 5 (1982) pp. 1378–1384.
Rosati, R. L., et al., J. Am. Chem. Soc., vol. 104, No. 15, 1982 pp. 4262–4264.
Kametani, T., et al., Chem. Pharm. Bull., vol. 31, 1983, pp. 2578–2582.
Narisada, M. et al., MEDI, Tues. Afternoon—Gen. Antibiotics, 13 (1986).
Herdewijn, P. et al., Nouveau J. De Chimie, vol. 7, N12-1983, pp. 691–695.

*Primary Examiner*—Robert Gerstl
*Attorney, Agent, or Firm*—John W. Harbour; Hesna J. Pfeiffer

[57] ABSTRACT

New antibacterial 6-amido-1-methylcarbapenems and process for their synthesis involving new azetidinone intermediates.

2 Claims, No Drawings

6-AMIDO-1-METHYL CARBAPENEMS

This is a continuation in part of the application Ser. No. 213,398 filed on Jun. 30, 1988 which is a continuation of application Ser. No. 371,358, filed Jun. 26, 1989, both now abandoned.

BACKGROUND OF THE INVENTION

1) Field of the Invention

This invention relates to new antibacterial 6-amido-1-methylcarbapenems and a process for their synthesis involving new azetidinone intermediates.

2) Brief Description of Disclosures in the Art

Carbapenem antibiotics, particularly imipenem (see U.S. Pat. Nos. 3,950,377 and 4,194,047) is well known for treating a broad spectrum of gram-negative and gram-positive bacterial infections.

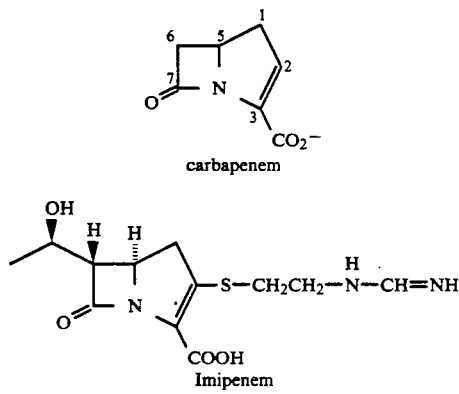

carbapenem

Imipenem

1-β-Methylcarbapenems, as described in the reference *Heterocycles*, 1984, Vol. 21, pp. 29–40 by D. H. Shih, F. Baker, L. Cama and B. G. Christensen, are extremely useful and effective broad spectrum antibiotics, useful against a wide variety of bacteria including gram-positive bacteria such as *S. aureus*, Strep. sp., *B. subtilis*, and gram-negative bacteria such as *E. coli*, Shigella sp., Enterobacter sp., Klebsiella sp., Proteus, Serratia and Pseudomonas sp.

However, all of the above antibacterial carbapenems utilize 6-substituents other than amido or substituted amido which are the 6-substituents of choice in penicillin, e.g.

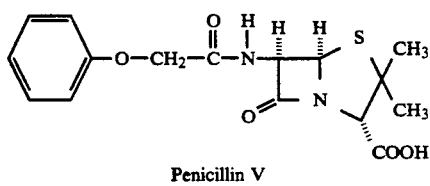

Penicillin V or the cephalosporins, e.g.

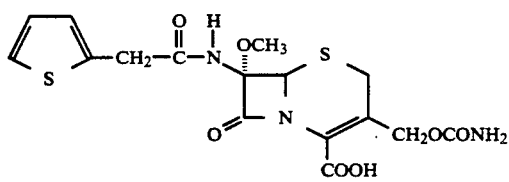

-continued
Cefoxitin

6-Amidocarbapenems and penams are known in the art as exemplified in the following references: U.S. Pat. No. 4,260,627; U.S. Pat. No. 4,206,219; U.S. Pat. No. 4,217,453; U.S. Pat. No. 4,218,459; U.S. Pat. No. 4,218,463; U.S. Pat. No. 4,277,482; and U.S. Pat. No. 4,298,741 to Merck & Co., Inc. which describe 1-H-6-amidocarbapenems and 1-methyl-6-aminocarbapenems; BE 887,618 and U.S. Pat. No. 4,347,355 to Abbott which describe 1,1'-diloweralkyl-6-amidocarbapenems; EPO Publication No. 040,494 and U.S. Pat. No. 4,348,264 to Pfizer which describes 1-hydroxy, acetoxy or 1,1'-oxo-carbapenems with 6-position conventional penicillin sidechains; EPO Publication Nos. 634,443 and 073,100 and U.S. Pat. No. 4,407,815 to Beecham which describe 1-H-6-amidocarbapenems and penams; Japanese Kokai 58 174 382 to Sanraku-Ocean Co. Ltd. which discloses 6-phthalimido-2-SR carbapenems; EPO Publication No. 045,198 to Takeda Chem. Ind. Ltd which discloses 1-alkyl-1'-alkoxycarbonyl, cyano or COR-substituted-6-amidocarbapenems; and EPO Publication No. 116,854 to Hofmann-LaRoche AG which discloses new azetidinone derivatives which can be used to prepare 1-H carbapenems.

Literature articles relating to 1-H-6-amidocarbapenems discussing problems in ring closures and ester deblocking reactions include: *Tetrahedron Letters*, 1982, 23 (15), 1545–1548; *Tetrahedron Letters*, 1982, 23 (50), 5339–5342; L. C. Blaszczak, Eli Lilly Co. Report "Joint Great Lakes and Central Regional Meeting", Western Michigan University, May 23–24, 1984; *J. Chem. Soc., Perkins Trans.* I, 1982, 2123–2129; *Helv. Chim. Acta*, 1982, 65, 1378–1384; *J. A. C. S.*, 1982, 104, 4262–4264.

New antibacterial compounds are constantly being searched for to enhance the potency, decrease the side effects of current existing carbapenem antibiotics. Thus far, 1-methyl-6-amidocarbapenems (I) have not been disclosed in the art.

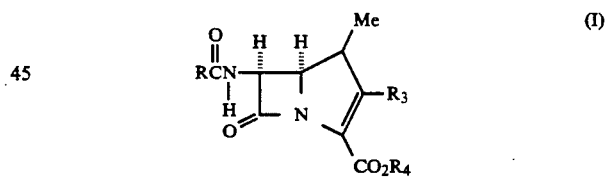

SUMMARY OF THE INVENTION

It has been found that a new class of compounds, 6-amido-1-methyl carbapenems exhibit antibacterial activity and can be synthesized from new 3-azido-azetidinone intermediates.

By this invention there is provided a compound of the structural formula:

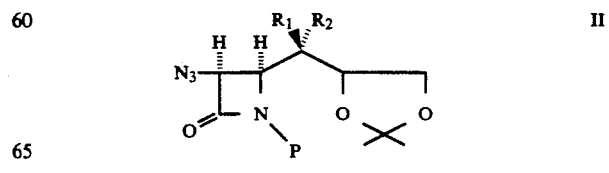

wherein $R_1/R_2$ is $H/CH_3$ or $CH_3/H$ and P is hydrogen or a nitrogen-protecting group removable by acid or basis hydrolysis, catalytic hydrogenation, or oxidative cleavage.

Further provided is a compound of the formula:

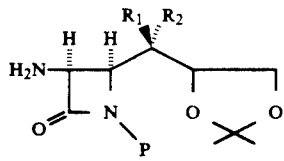   III wherein $R_1/R_2$ is $H/CH_3$ or $CH_3/H$ and P is hydrogen or a nitrogen-protecting group removable by acid or basis hydrolysis, catalytic hydrogenation, or oxidative cleavage.

Also provided is a compound of the structural formula:

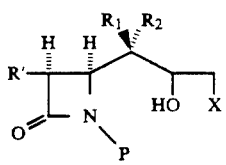   IV wherein $R_1/R_2$ is $H/CH_3$ or $CH_3/H$; P is hydrogen or a nitrogen-protecting group removable by acid or basic hydrolysis, catalytic hydrogenation, or oxidative cleavage; R' is $N_3$, $NH_2$, phthalimido, or NHCOR", where R" is benzyl, phenoxymethyl, thienylmethyl, allyloxy or p-nitrobenzyloxy; and X is OH, OP, $OCOCH_3$, phenyl, or pyridyl, where P is a hydroxyl protecting group.

Furthermore, there is provided a compound of the formula:

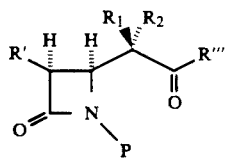   V wherein $R_1/R_2$ is $H/CH_3$ or $CH_3/H$; P is hydrogen or a nitrogen-protecting group removable by acid or basis hydrolysis, catalytic hydrogenation, or oxidative cleavage; R' is $N_3$, $NH_2$, phthalimido, or NHCOR", where R" is benzyl, phenoxymethyl, thienylmethyl, allyloxy or p-nitrobenzyloxy; and R''' is H, OH, $OC_1$-$C_4$, O-allyl, O-benzyl, O-p-nitrobenzyl, or the like, $SR^6$, or $CH_2X$; wherein $R^6$ is selected from phenyl or 2-pyridyl, and wherein X is OH, OP, $OCOCH_3$, phenyl or pyridyl, where P is a hydroxyl protecting group.

Also provided is a compound of the formula:

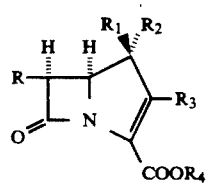   VI wherein $R_1/R_2$ is $CH_3/H$ or $H/CH_3$; $R_3$ is H, $CH_2X$ wherein X is halo; OH or

wherein $R^5$ is substituted or unsubstituted $C_1$-$C_3$ alkyl, $C_6$-$C_{10}$aryl or 5-6 membered heteroaryl; phenyl or substituted phenyl; or $NH_2$; $R_4$ is an alkali metal, conventional carboxyl protecting group or pharmaceutically acceptable or biolabile group known in the art; and R is selected from the substituents:

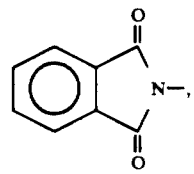   (a)

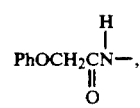   (b)

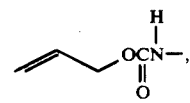   (c)

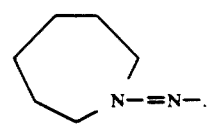   (d)

BRIEF DESCRIPTION OF THE INVENTION AND PREFERRED EMBODIMENTS

The invention can be readily understood by reference to the following flow sheets which exhibit the processes for the synthesis of the instantly claimed compounds which are the preferred embodiments.

FLOW SHEET A

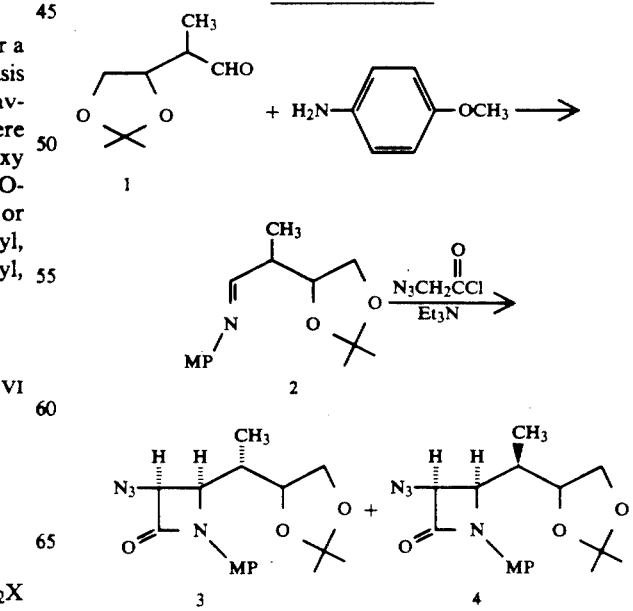

-continued
FLOW SHEET A
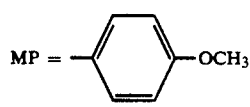
FLOW SHEET B
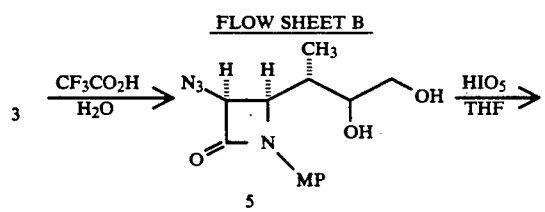
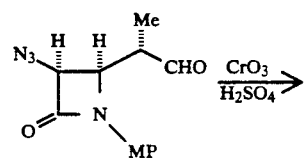
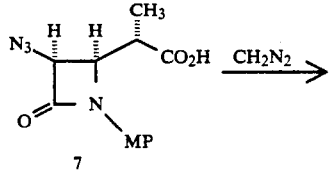
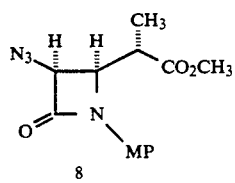
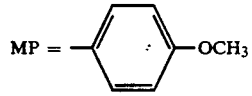
FLOW SHEET C
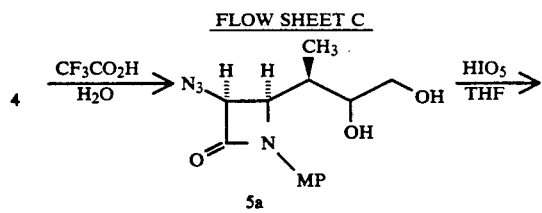
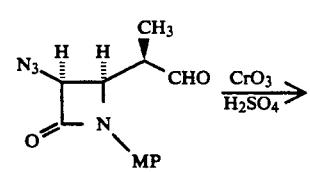
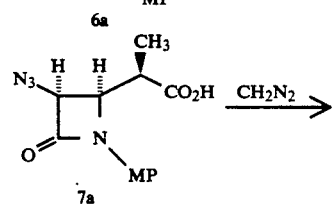
FLOW SHEET C (continued)
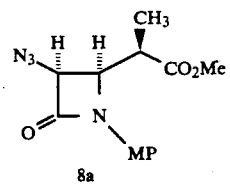
MP = 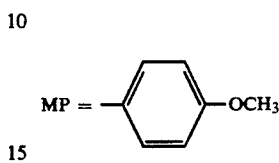
FLOW SHEET D
Mixture 3 + 4 $\xrightarrow{H_2}{PtO_2}$
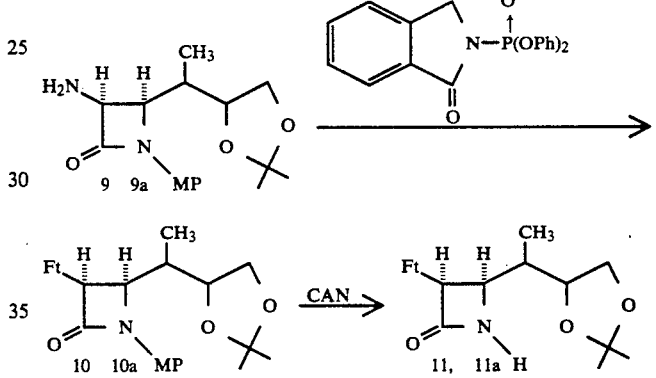
MP = 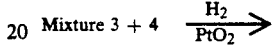   Ft = (phthalimidoyl)
CAN = $(NH_4)_2Ce(NO_3)_6$
FLOW SHEET E
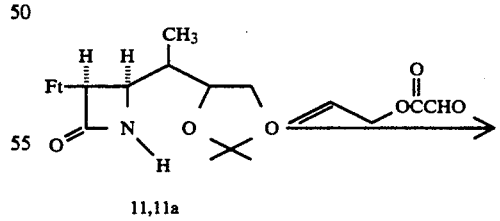
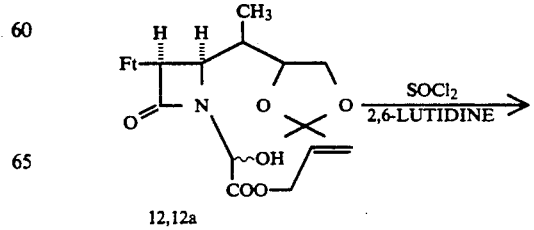

-continued
FLOW SHEET E
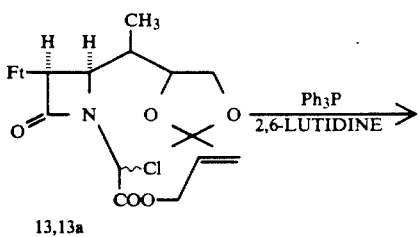
13,13a
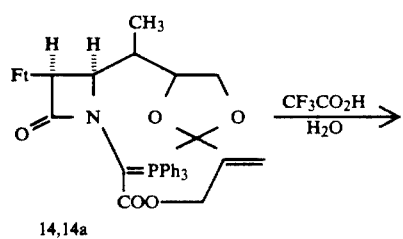
14,14a
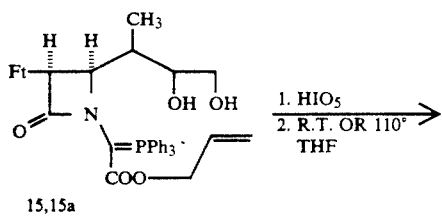
15,15a
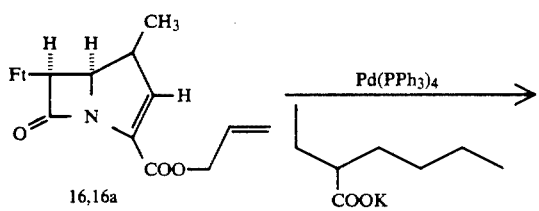
16,16a
17,17a
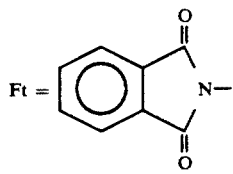
FLOW SHEET F
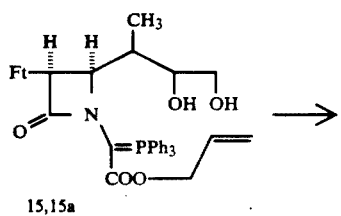
15,15a
-continued
FLOW SHEET F
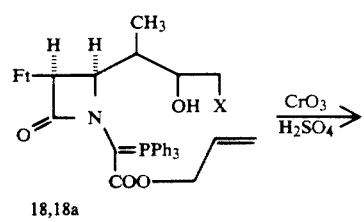
18,18a
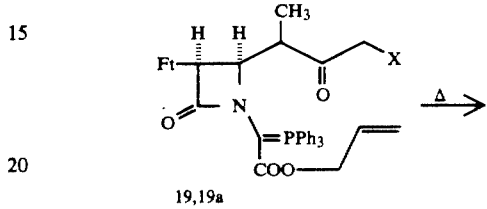
19,19a
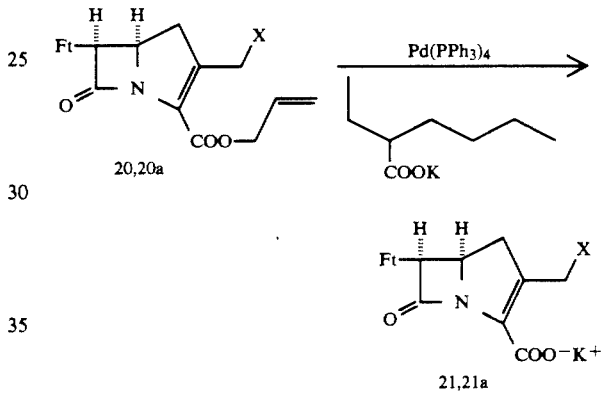
20,20a       21,21a
X = —OH, —OSi(Me)₂CMe₃, —OAc, HALOGEN, —SR, etc.
FLOW SHEET G
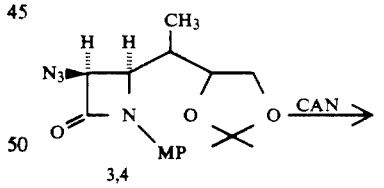
3,4
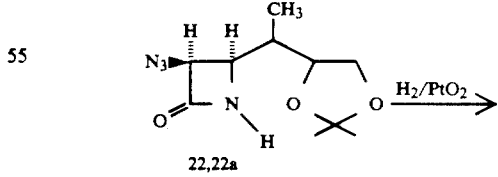
22,22a
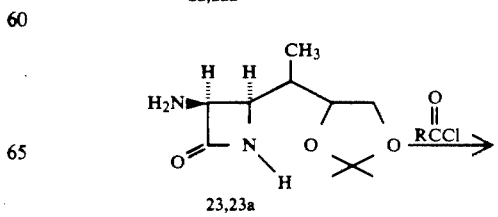
23,23a 5,138,050
-continued
FLOW SHEET G
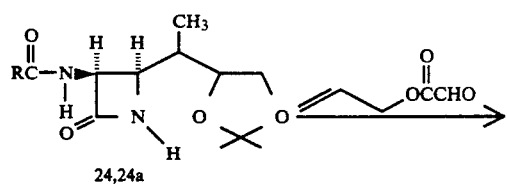
24,24a
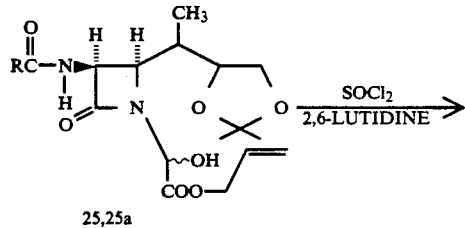
25,25a
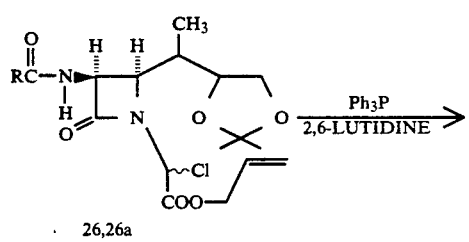
26,26a
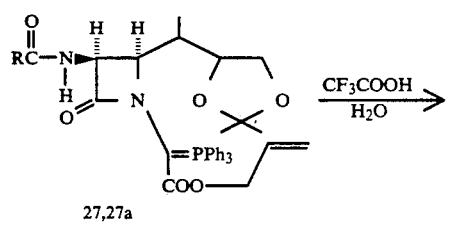
27,27a
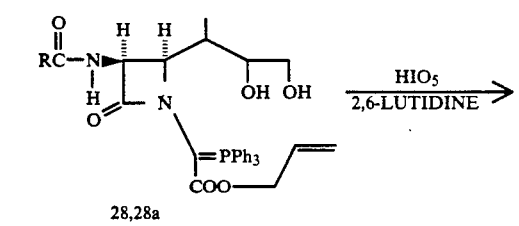
28,28a
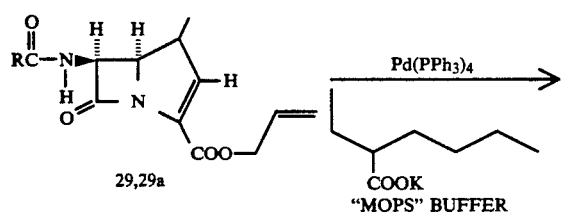
29,29a
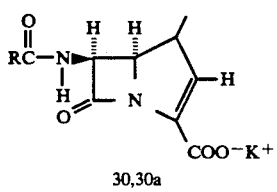
30,30a
CAN = (NH$_4$)$_2$Ce(NO$_3$)$_6$
-continued
FLOW SHEET G
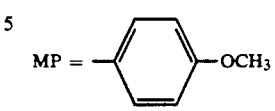
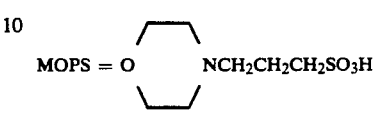
FLOW SHEET H
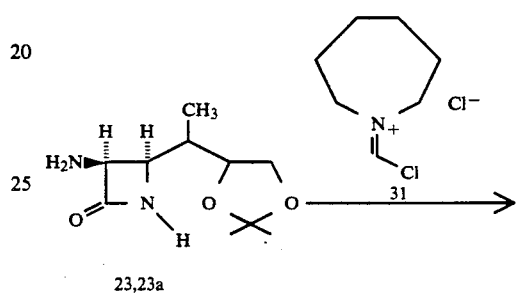
23,23a
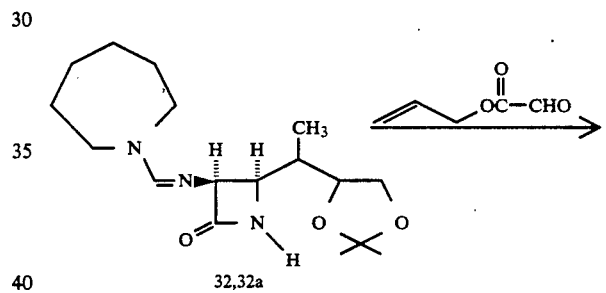
32,32a
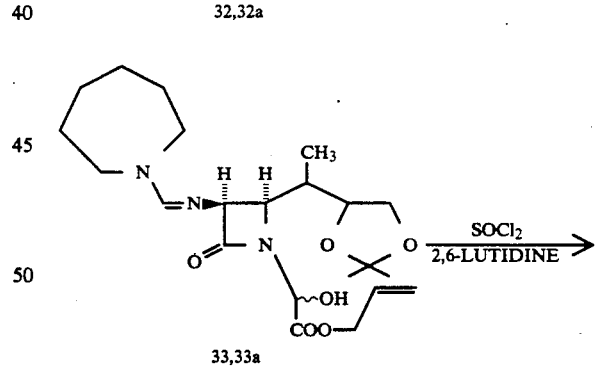
33,33a
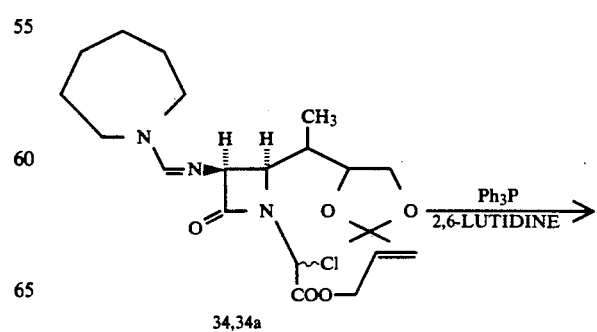
34,34a -continued
FLOW SHEET H
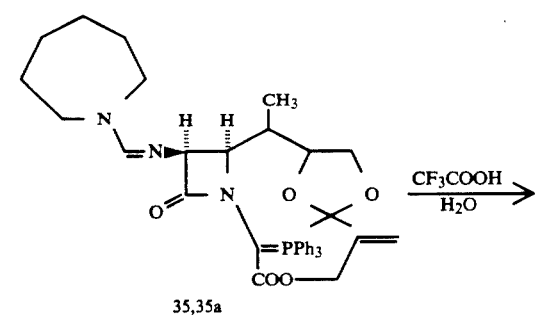
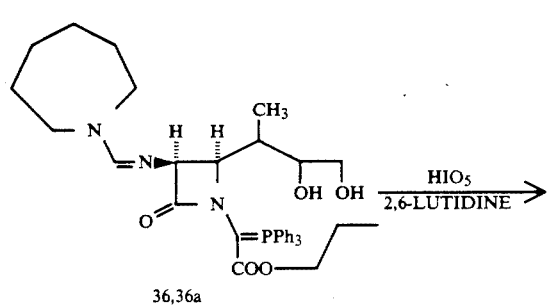
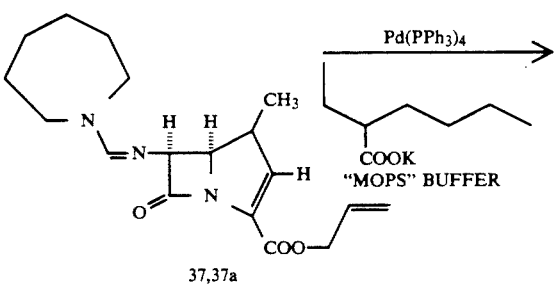
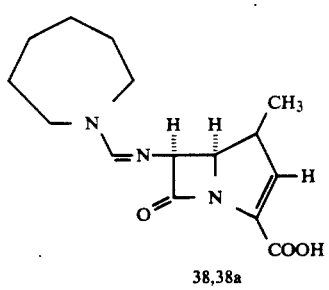
FLOW SHEET I
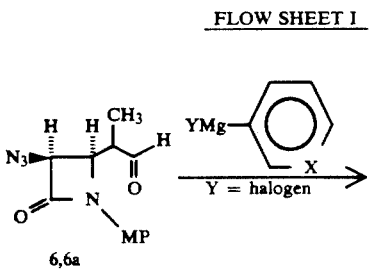
-continued
FLOW SHEET I
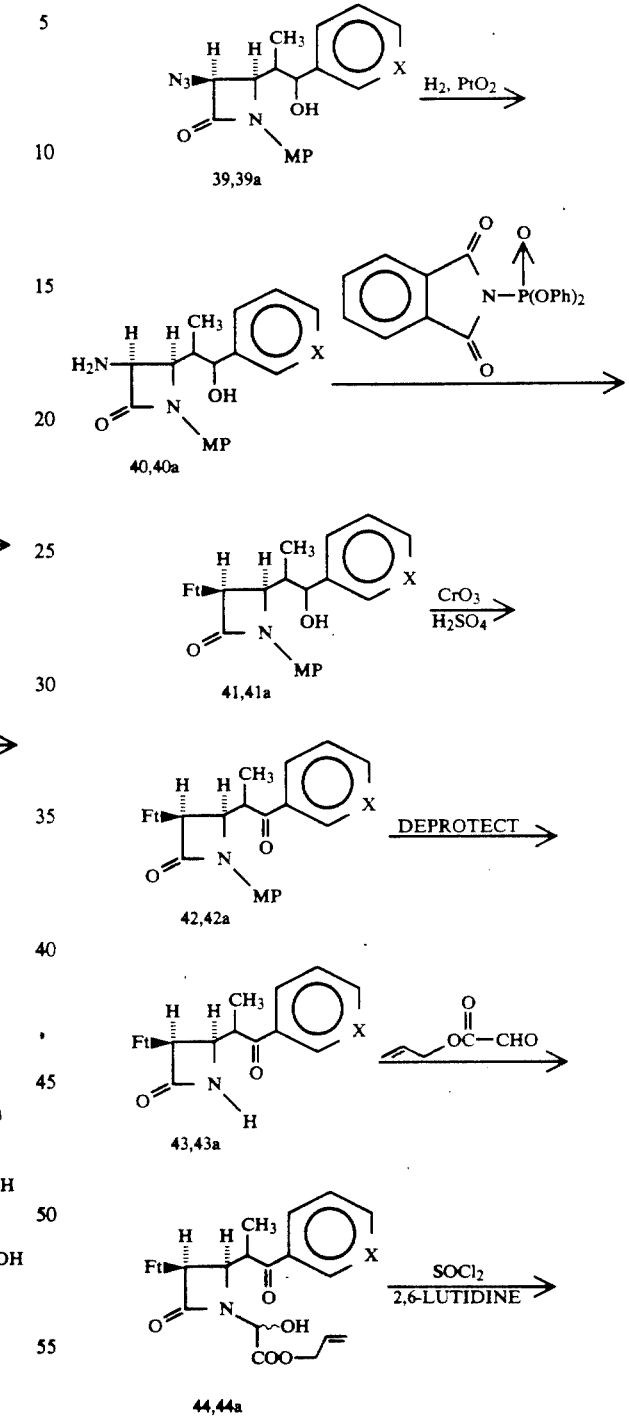
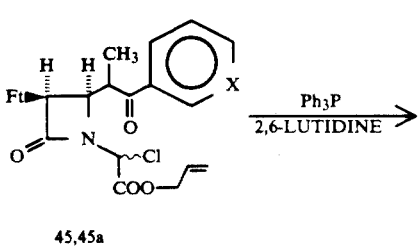

-continued
FLOW SHEET I

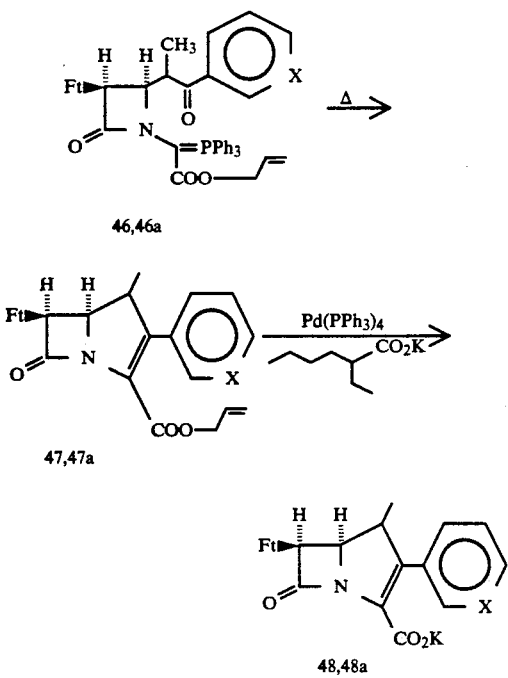

X = CH, N

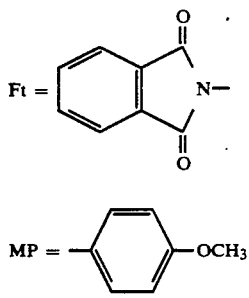

Flow Sheet A illustrates the synthesis of the azido intermediates 3 and 4 which can be used to prepare all of the subsequent intermediates in the invention process and the title compounds. Most noteworthy are the phthalimido intermediates 11, 11a which are subsequently used in Flow Sheet D to prepare some of the title compounds, and also the azido aldehydes 6, 6a which are used in Flow Sheet I for synthesis of the titled carbapenems.

In general, unless otherwise indicated, a compound followed by the letter "a" is in the beta methyl configuration (see compound 8a, showing an asterisked beta-methyl); the absence of "a", e.g. compound 8, usually indicates the corresponding alpha form.

In the foregoing formulas IV to VI wherein $R_3$ is —$CH_2X$ and X is $O(C=O)R^5$, $R^5$ is substituted or unsubstituted $C_1$-$C_3$ alkyl; $C_6$-$C_{10}$ aryl; or "heteroaryl", and by that term is meant a 5–6 membered unsaturated ring system containing 1–3 oxygen, sulfur or nitrogen atoms, including pyridyl, thiazolyl, thiadiazolyl, isothiazolyl, thienyl, and the like. Substituents or the above alkyl, aryl or heteroaryl groups include: halo, $C_1$-$C_4$ alkyl, $C_1$-$C_4$alkoxyl, nitro, trifluoromethyl, cyano, amino, carboxyl, and the like; $R'$ is $N_3$, $NH_2$, phthalimido or NHCOR'', where R'' is benzyl, phenoxymethyl, thienylmethyl, allyloxy or p-nitrobenzyloxy; and R''' is H, OH, $OC_1$-$C_4$, O-allyl, O-benzyl, O-p-nitrobenzyl, or the like, $SR^6$, or $CH_2X$; wherein $R^6$ is selected from phenyl or 2-pyridyl, and wherein X is OH, OP, $OCOCH_3$, phenyl or pyridyl, where P is a hydroxyl protecting group.

The above compounds can be made by the procedures described in the following Examples herein or by closely analogous procedures which will be obvious to one skilled in the art.

Referring to Flow Sheet A, the known starting aldehyde 1 is reacted with a suitable amine, e.g. aniline, benzylamine, 2,4-dimethoxybenzylamine, and preferably p-methoxyaniline. This reaction may be carried out in the presence of a dehydrating agent, for example, magnesium sulfate in solvents like ether for 1–3 hours at ambient temperature to produce the imine 2 (See Ex. 1).

The imine 2, can be reacted overnight at from −78° C. to about room temperature with azidoacetyl chloride in solvents like ether or methylene chloride in the presence of a tertiary amine such as triethylamine or diisopropylethylamine or the like to produce the alpha azetidinone 3 and the beta azetidinone 4, which can be separated by chromatographic techniques.

These separated isomers may be reacted in similar schemes to produce desired intermediates as indicated in Flow Sheets B and C. Firstly, both isomers, alpha azetidinone 3 and beta azetidinone 4, can be treated with trifluoroacetic acid/water at −20° C. to room temperature for 1–2 hours to form the respective isomeric diols 5 and 5a. the latter diol structure was confirmed by X-ray analysis (See Exs. 3, 4). Subsequently, each isomer may be treated with periodic acid in solvents like tetrahydrofuran (THF) at room temperature (RT) for 0.5–2 hours to form the corresponding aldehydes 6 and 6a (See Exs. 5, 6). The isomeric aldehydes 6 and 6a may be subjected to Jones oxidation for 1–2 hours at about 0° C. in solvents like acetone to form the respective carboxylic acids 7 and 7a (See Exs. 7, 8). Finally, in this sequence, carboxylic acids 7 and 7a are esterified with diazomethane for 1–3 hours at room temperature in solvents like ethyl acetate to the methyl esters 8 and 8a. (See Exs. 9, 10). The purpose of compounds 7, 7a, 8, 8a is to provide additional chemical support for the aforementioned synthesis and to generate alternative, useful synthetic intermediates applicable for the synthesis of this instant invention and other classes of β-lactam antibiotics.

Alternatively to reacting the isomers, alpha azetidinone 3 and beta azetidinone 4 as described above, both azido isomers, 3 (alpha) and 3a (beta) can be catalytically hydrogenated in solvents like ethyl acetate for 8–18 hours with platinum oxide at room temperature and 45 psi to the corresponding free primary amines 9 (alpha) and 9a (beta) (See Exs. 11, 12). The amino groups of 9 and 9a can be converted to the phthalimidoyl moiety by treatment with N-diphenyldiphosphonophthalimide in refluxing anhydrous toluene for 2–5 hours forming compounds 10 (alpha) and 10a (beta) (See Exs. 16, 17). Removal of the N-protecting group with ceric ammonium nitrate (CAN) at 0° C. for 0.5–1 hour in acetonitrile leads to the N-H deprotected compounds 11 and 11a (See Exs. 19, 20).

Referring to Flow Sheet E, treatment of 11 and 11a with allylglyoxalate in anhydrous methylene chloride in the presence of anhydrous magnesium sulfate under nitrogen ($N_2$) at room temperature for 1–4 hours leads to the corresponding hydroxy allyl carboxylic esters 12 and 12a (See Exs. 25, 26). Treatment of 12, 12a with thionyl chloride and a proton acceptor such as 2,6-lutidine at −40° C. for 0.5-2 hours in anhydrous THF under nitrogen leads to the corresponding chloro compounds 13, 13a (See Exs. 30, 32). Chloro compounds 13 and 13a may be treated for 3-10 hours in situ with triphenylphosphine in anhydrous DMF at 80° C. to yield the phosphoranes 14, 14a, (See Exs. 31, 33). In turn phosphoranes 14 and 14a may be treated with trifluoroacetic acid/water at −20° C. to 0° C. for 1-2 hours to yield the dihydroxybutyl compounds 15, 15a (See Exs. 36, 37). The dihydroxybutyl moiety is utilized to form in situ the aldehyde which cyclizes to a five membered ring of the carbapenem. Thus, treatment of 15, 15a with periodic acid in tetrahydrofuran at room temperature for 0.25-1 hour or, refluxing in toluene at 110° C. for 1-18 hours, yields the ring closed carbapenems 16, 16a (See Exs. 40, 42). Deblocking of the carboxylic allyl ester with tetrakis (triphenylphsophine) palladium (O) and potassium 2-ethyl hexanoate in 1:1 methylene chloride/ethyl acetate at room temperature under $N_2$ for 1-2 hours yields the title compounds 17, 17a (See Exs. 45, 46).

Referring to Flow Sheet F, the phthalimido phosphoranes 15, 15a, contain in omega hydroxyl group which can be derivatized by acylation, e.g., acylated with acetyl chloride, in the presence of a suitable hydrogen acceptor such as pyridine, 2,6-lutidine, triethylamine, dimethyldodecylamine, and the like, to form the omega acetate compounds, 18, 18a, where X is, for example OAc (See Ex. 48). X can further be an O-silyl protecting group OSiR$^1$R$^2$R$^3$, being conventional in the carbapenem art, e.g. OSi(Me$_2$)CMe$_3$ (See Ex. 49).

These compounds, phthalimido phosphoranes 15, 15a, can be oxidized to the corresponding keto forms 19, 19a with Jones Reagent, i.e. chromic acid/sulfuric acid in acetone solvent at room temperature for 0.5-2 hours, (See Exs. 50, 51). Also compound 19 when X=OH can be prepared from 19 where X=OSi(Me$_2$)CMe$_3$ by desilylating with tetrabutylammonium fluoride and acetic acid in anhydrous THF at room temperature under $N_2$ (See Ex. 53) for 8-48 hours.

Treatment of keto phthalimido phosphoranes 19, 19a at 110° C. in toluene for 3-48 hours affords the ring closure to the corresponding carbapenems 20, 20a (See Exs. 54, 55, 56). X may be —OH or —OP, where P is a conventional hydroxy protecting group, such as acetyl, dimethyl-t-butylsilyl, benzyl and p-methoxybenzyl or the like. Subsequent removal of the allyl protecting group on carbapenem 20, 20a yields the title compounds 21, 21a (See Ex. 58) where X=OAc. The conditions for removing the allyl group include contacting the allyl ester in an inert solvent, such as a 1:1 mixture of CH$_2$Cl$_2$/EtOAc at room temperature with tetrakis (triphenylphosphine) palladium and potassium or sodium 2-ethylhexanoate exchange reagent, stirring for about one hour and isolating by conventional means the potassium or sodium salt of the deblocked carboxylic acid.

Referring to Flow Sheet G, this process illustrates the conversion of the azide intermediates 3, 4 to title carbapenems 30, 30a. Treating azide intermediates 3, 4 with ceric ammonium nitrate for 0.5-2 hours at 0° C. in aqueous acetonitrile to deblock the ring amide nitrogen protecting group yields compounds 22, 22a (See Ex. 22). Subsequent catalytic hydrogenation of the azido group in compounds 22, 22a using PtO$_2$ yields the amino derivatives 23, 23a (See Ex. 13). Conversion of the azido group to an amino group permits subsequent conversion to an amido group on what is to be the 6-position of the carbapenem. This conversion is accomplished by acylation of the amine with an acylating agent and a conventional basic reagent at −20° C. to 0° C. to give a resulting amido side chain. Acylation of amino derivatives 23, 23a to provide, for example, an allyloxy carbonyl derivative can be carried out with allylchloroformate in anhydrous CH$_2$Cl$_2$ at 0° C. for 1-8 hours under nitrogen with pyridine as a proton acceptor to yield compounds 24, 24a (Exs. 23, 24). Such side chains are known in the penicillin/cephalosporin art but not the carbapenem art.

Representative examples of suitable amido side chains are taken from the Merck Index, Tenth Edition, published by Merck & Co. Inc., hereby incorporated by reference for this particular purpose. Representative examples include 2-amino-phenylacetamido, 2-amino-p-hydroxyphenylacetamido, mandelamido, 3,5-dichloro-4-pyridon-1-yl-acetamido, 1-H-tetrazolylacetamido, 2-amino-4-thiazolyl-alphamethoxyimino-acetamido, cyanomethylthioacetamido, 4-ethyl-2,3-dioxo-1-piperazinyl-carbonylamino-alpha-p-hydroxyphenyl-acetamido, 2-aminomethylphenylacetamido, carbamoylcarboxymethylene-1,3-dithietane carboxamide, 2-thienylacetamido, butylmercaptoacetamido, phenylacetamido, 4-amino-4-carboxybutyramido-, allymercaptoacetamido, gamma-chlorocrotylmercaptoacetamido, phenoxyacetamido, 2-(1,4-cyclohexadien-1-yl)-2-aminoacetamido, alpha-sulfoacetamido, 2-amino-4-thiazolyl-alphacarboxyisopropoxyiminoacetamido, 2-furyl-a-methoxyimino-acetamido, and the like. Preferred as R are (a) phenoxymethyl, (b) allyloxy, (c) p-nitrobenzyloxy, (d) phenylmethyl, and (e) 2-thienylmethyl.

Following acylation as shown in Flow Sheet G, the basic carbapenem structure must be formed to complete synthesis of the title compound. As a first step, treatment of 24, 24a with allylglyoxalate in anhydrous methylene chloride with powdered 4 Å molecular sieves for 5-24 hours yields compounds 25, 25a (See Exs. 27, 28). Subsequently, treating 25, 25a with thionyl chloride and 2,6-lutidine in anhydrous THF at −40° C. for 0.5-2 hours yields the chloro analogs 26, 26a. Contacting the chloro compounds 26, 26a in situ with triphenylphosphine/2,6-lutidine in anhydrous DMF at 80° C. for three hours yields the triphenylphosphoranes 27, 27a (See Exs. 33, 34). Treatment of 27, 27a with trifluoroacetic acid/water at −20° C. for 0.5-4 hours yields the dihydroxy compounds 28, 28a (see Exs. 38, 39). Oxidation of 28, 28a, in anhydrous methylene chloride at 45°-47° C. for 15-30 minutes, with periodic acid/2,6-lutidine proceeds with concomitant cyclization of the resulting aldehyde to afford carbapenems 29 and 29a (See Exs. 43, 44). Deblocking of the allyl group as described above affords the title carboxylic acid potassium or sodium salts 30, 30a (See Ex. 47).

Referring to Flow Sheet H, the amines 23, 23a from Flow Sheet G can be reacted with hexahydro-1H-azepinium chloride, 31, prepared from 1-(formyl)-hexahydro-1H-azepine and oxalyl chloride, in anhydrous CH$_2$Cl$_2$ at 0° for 1-3 hours in the presence of triethylamine to yield imidates 32, 32a (See Ex. 60). Treating the ring amido nitrogen with allylglyoxalate and anhydrous magnesium sulfate in anhydrous methylene chloride under nitrogen ($N_2$) at room temperature yields hydroxy allyl carboxylic esters 33, 33a (See Ex. 61). Subsequent treatment of compounds 33, 33a with thionyl chloride at −40° C. in anhydrous THF for 0.5-2 hours followed in situ with triphenylphosphine/2,6-lutidine in anhydrous DMF at 80° C. for 3-10 hours yields the phosphoranes 35, 35a by way of compounds 34, 34a (See Ex. 62). Dioxolane ring opening of compound 35, 35a with trifluoroacetic acid and water at −20° C. for 0.5-5 hours yields 36, 36a (See Ex. 63). Opening the dioxolane ring permits a subsequent closure of the fused 5-membered ring by periodic acid oxidation in THF at room temperature to produce carbapenem 37, 37a (See Ex. 64). Carbapenems 37, 37a are finally deblocked of the allylcarboxyl group yielding the title compounds 38, 38a (See Ex. 65).

Referring to Flow Sheet I, the aldehydic azetidinones 6, 6a can be treated at −78° C. in anhydrous THF for 0.5-2 hours with aryl Grignard reagents which may be selected from phenylmagnesium bromide and 3-pyridyl magnesium bromide, and the like, to form the alcohols 39, 39a (See Ex. 66). Subsequent catalytic hydrogenation with $PtO_2$ at room temperature and 45 psi in methanol or ethylacetate converts the azide of alcohol 39, 39a to the amine compounds 40, 40a (See Ex. 15). Treatment of amine compounds 40, 40a with diphosphonophthalimidate in refluxing anhydrous toluene for 2-8 hours yields the phthalimido derivatives 41, 41a (See Ex. 18). Upon obtaining the phthalimido derivatives 41, 41a, a fused ring may next be formed on the azetidinone to result in a carbapenem. As a first step to form the fused ring, phthalimide derivatives 41, 41a are reacted in a Jones oxidation with $CrO_3/H_2SO_4$ in acetone at room temperature for 1-5 hours to yield 42, 42a (See Ex. 52). Subsequently, the N-protecting group may be removed with CAN to yield 43, 43a (See Ex. 22). Aminal formation with allylglyoxalate in anhydrous methylene chloride under nitrogen at room temperature for 2-10 hours yields 44, 44a (See Ex. 29). Treatment of compounds 44, 44a with thionyl chloride and a proton acceptor such as 2,6-lutidine at −40° C. leads to the chloro compounds 45, 45a. Subsequent in situ treatment with $Ph_3P$/2,6-lutidine in anhydrous DMF at 80° C. forms 46, 46a (See Ex. 35). Final ring closure to 47, 47a is afforded by heating compounds 46, 46a in toluene at 110° C. for 3-20 hours. (See Ex. 57). Deprotection of the allyl ester is accomplished as before to provide carbapenems 48, 48a (See Ex. 58).

The novel compounds in the different chemical classes of the present disclosure are believed to be valuable antibiotics active against various Gram-positive and Gram-negative bacteria and accordingly find utility in human and veterinary medicine. Representative pathogens which are sensitive to antibiotics I include: *Staphylococcus aureus*, and *Escherichia coli*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 250 mg to 1000 mg. In parenteral administration, the unit dosage amount is usually the pure compound I in sterile water solution or in the form of a soluble powder intended for solution.

EXAMPLE 1

(±)-1-(4'-Methoxyphenyl)-3S-Azido-4R-[1-[4-(2,2-Dimethyl-1,3-Dioxolanyl)Ethyl]]Azetidin-2-one, 3 and 4

To a vigorously stirred solution of 4-anisidine (21.3 G, 0.173M) in 300 mL of anhydrous ethyl ether were added anhydrous magnesium sulfate (50 G), and 2-[4'-(2',2'-dimethyldioxanyl)] propanal, 1 (27.2 G, 0.172M) prepared according to the procedure described in *Tetrahedron Letters* Vol. 21, pp. 685-688, by B. Ganem et al., and incorporated by reference for this particular purpose. This mixture was stirred under nitrogen at room temperature for 1.5 hours. Solids were filtered and washed with 3×50 mL of ether. The filtrate was concentrated in vacuo at room temperature to give the desired Schiff base, 2, which was used immediately without further purification. Spectral data for 2:

NMR(CDCl$_3$): $\delta$1.29(d, J=7 Hz, CH$_3$) 1.39 & 1.45(2 singlets, acetonide CH$_3$'s) 2.67-2.81(M. CHCH$_3$) 3.83(s, OCH$_3$) 6.88-7.09(phenyl H's) 7.86(d, J=5 Hz, CH=N)

IR(Thin Film): 1653 cm$^{-1}$ (C=N)

EXAMPLE 2

Triethylamine (28.98 mL, 0.208M) was added dropwise to a well stirred solution of azidoacetylchloride (18.18 mL, 0.208M) in anhydrous ethyl ether (750 mL) at −78° C. under nitrogen. A voluminous white precipitate formed. This reaction mixture was stirred for 1 hour at −78° C. A solution of the above prepared Schiff base in anhydrous ethyl ether (250 mL) was then added over 10 minutes at −78° C. under nitrogen. The mixture was stirred at −78° C. for 2 hours and was allowed to warm to room temperature over night. The reaction mixture was washed with 3×150 mL of water, 150 mL of saturated sodium chloride, and dried over anhydrous magnesium sulfate. Solvent removal gave a brown oil, which was chromatographed on silica gel using 2:3 ether:petroleum ether (30°-60° C.) as solvent to give first (±)-1-(4'-methoxyphenyl)-[4-(2,2-dimethyl-1,3-dioxolanyl)ethyl] 3(S)-azido-4(R)-(1S)-azetidin-2-one, 3 (20.3 G, 34%) as solid mixture, spectral data:

NMR(CDCl$_3$): 1.05(d, J=7 Hz, CH$_3$) 1.25 & 1.47(2 singlets, acetonide CH$_3$'s) 3.82(s, OCH$_3$) 4.24-4.34(dd, J=5 & 9 Hz, H-4) 4.89(d, J=5 Hz, H-3) 6.87-7.56(phenyl H's)

and then (±)-1-(4'-methoxyphenyl)-3S-azido-(4R)-(1R)-[(4R)-(2,2-dimethyl-1,3-dioxolanyl)ethyl]-azetidin-2-one 4 (14.3 G, 24%), which was crystallized from ethyl acetate/ether as colorless crystals melting at 126°-127° C. Spectral data:

NMR(CDCl$_3$): 1.0(d, J=7 Hz, CH$_3$) 1.41 & 1.49(2 singlets, acetonide CH$_3$'s) 2.30-2.44(m, CHCH$_3$) 3.88(s, OCH$_3$) 4.40-4.50(dd, J=5.5 & 7.5 Hz, H4) 4.99(d, J=5.5 Hz, H3) 6.92-7.39(phenyl H's).

MS: m/e 346(M+) Calculated for C$_{17}$H$_{22}$N$_4$O$_4$=346.1641 Found =346.1641

EXAMPLE 3

(±)-1-(4'-Methoxyphenyl)-3S-Azido-4R-[(2R,3S)&(2S,3S)-3-(1,2-Dihydroxybutyl)]-Azetidin-2-one, 5

A diastereomeric mixture of (±)-1-(4'-methoxyphenyl)-3S-azido-4R-[(1S)-4-(2,2-dimethyl-1,3-dioxolanyl)ethyl]-azetidin-2-one 3 (1.038 G, 3 mM) was added to a stirred mixture of trifluoracetic acid and water (9:1; 10 mL). This reaction mixture was stirred 15 minutes at ambient temperature. Acid was neutralized carefully with aqueous saturated sodium bicarbonate solution. This mixture was extracted with 3×20 mL of ethyl acetate. The combined organic layers were dried over anhydrous magnesium sulfate. Solvent removal gave a crude product, which was chromatographed on silica gel using 1:3 cyclohexane:ethyl acetate as solvent. Less polar (±)-1-(4'methoxyphenyl)-3S-azido-4-R-[(2S,3S)-3-(1,2-dihydroxybutyl)]-azetidin-2-one, 5, 650 mG (71%) was obtained as white solid, recrystallized from ether, melting at 128.5°-129.5° C. The single crystal X-ray analysis confirmed the assignment of the relative configuration of all the chiral centers. In addition, more polar diastereomer (5) (±)-1-(4'-methoxyphenyl)-(3S)-azido-4R-[(2R,3S)-3-(1,2-dihydroxybutyl)]-azetidin-2-one, (50 mG, 5.5%) was obtained as thick oil.

NMR(CDCl$_3$): 1.04(d, J=7 Hz, CH$_3$) 2.08-2.22(m, CHCH$_3$) 3.82(s, OCH$_3$) 4.36-4.46(dd, J=5 & 8 Hz, H4) 4.91(d, J=5 Hz, H3) 6.90-7.51(phenyl H's)

MS: m/e 306(M+) 307(M+H) 612(2M+) 613(2M+H)

EXAMPLE 4

Similar treatment of (±)-1-(4'-methoxyphenyl)-3S-azido-(4R)-(1R),-[(4R)-(2,2-dimethyl-1.3-dioxolanyl)ethyl]azetidin-2-one 4 with aqueous trifluoroacetic acid gave 75% of (±)-1-(4'-methoxyphenyl)-3S-azido-4R-(2R,3R)-(3-(1,2-dihydroxy)butyl]azetidin-2-one 5a as amorphous powder.

IR(Thin Film): 2128 cm$^{-1}$ (—N$_3$); 1753 cm$^{-1}$ ($\beta$-Lactam CO)

NMR(CDCl$_3$): 0.97(d, J=7 Hz, CH$_3$); 2.16-2.42 (m, CHCH$_3$) 4.48-4.58(dd, J=5.5 & 8 Hz, H4) 4.93(d, J=5.5 Hz, H3) 6.90-7.40(phenyl H's)

EXAMPLE 5

(±)-1-4'-Methoxyphenyl)-3S-Azido-(4R)-(1S)-[Carboxaldehydoethyl]Azetidin-2-one, 6

A solution of periodic acid (456 mG, 2 mM) in 5 mL of anhydrous tetrahydrofuran was added to a solution of (±)-1-(4'-methoxyphenyl)-3S-azido-4R-[(2S,3S)-3-(1,2-dihydroxybutyl)]azetidin-2-one, 5, (612 mG, 2 mM) in 10 mL of anhydrous tetrahydrofuran. After strrring for 15 minutes at ambient temperature under nitrogen, a white solid separated out. The reaction mixture was diluted with 30 mL of ethyl acetate, and washed with 2×5 mL of saturated aqueous sodium bicarbonate solution, 5 mL of saturated sodium chloride solution. After drying over anhydrous magnesium sulfate, the organic phase was concentrated in vacuo at room temperature to give 540 mG (98.5%) of (±)-1-(4'-methoxyphenyl)-3S-azido-(4R)-[(1s)-carboxaldehydo-ethyl]azetidin-2-one 6, melting at 97°-8° C.

NMR(CDCl$_3$): 1.32(d, J=7 Hz, CH$_3$) 3.10-3.30(m, CHCH$_3$) 3.83(s, OCH$_3$) 4.70-4.78(dd, J=5 & 5 Hz, H4) 5.04(d, J=5 Hz; H3) 6.90-7.34(phenyl H's) 9.86(s, CHO)

This aldehyde 6 was also obtained from the diastereomeric (±)-1-(4'-methoxyphenyl)-3R-azido-4R-[(2R,3S)-3-(1,2-dihydroxybutyl)]azetidin-2-one, (5), by similar treatment with periodic acid in comparable yield.

Chromatography of this aldehyde on silica gel using 4:1 ether:petroleum ether as solvent gave a mixture α-methyl, 6, and β-methyl, 6a aldehydes owing to the isomerization of the α-methyl substituent.

EXAMPLE 6

(±)-1-(4'-Methoxyphenyl)-3S-azido-4R-[(1R)-Carboxaldehydoethyl]Azetidin-2-one, 6a Similar treatment of (±)-1-(4'-methoxyphenyl)-3S-azido-R-[(2R,3R)-[3-(1,2-dihydroxy)butyl)]azetidin-2-one, 5a with periodic acid gave 97% of (±)-1-(4'-methoxyphenyl)-3S-azido-4R-[-(1R)-carboxaldehydoethyl]azetidin-2-one, 6a.

NMR(CDCl$_3$): 1.24(d, J=8 Hz, CH$_3$) 2.88-3.04(M, $\overline{CHCH_3}$) 3.81(s, OCH$_3$) 4.78-4.84(dd, J=5 & 5 Hz, H4) 5.03(d, J=5 Hz, H3) 6.88-7.34(phenyl H's)

IR(Thin Film): 2130 cm$^{-1}$ (N$_3$) 1778 cm$^{-1}$)(β-Lactam CO) 1739 cm$^{-1}$)(CHO)

Chromatography of this aldehyde on silica gel using 4:1 ether:petroleum ether as solvent gave the same mixture of α- & β-methylaldehydes as mentioned above.

EXAMPLE 7

(±)-1-(4'-Methoxyphenyl)-3S-Azido-4R-[(1S)-Carboxyethyl]Azetidin-2-one, 7

To a stirred solution of (±)-1-(4'-methoxyphenyl)-3S-azido-[(4R)-[(1S)-carboxaldehydoethyl]azetidin-2-one, 6, (411 mG, 1.5 mM) in 5 mL of acetone at 0° was added 0.40 mL of 4 molar Jones Reagent. The reaction mixture was stirred at 0° C. for 15 minutes. A green gummy solid separated out. The reaction mixture was diluted with 25 mL of ethylacetate and washed with 3×10 mL of saturated sodium chloride solution, and dried over anhydrous magnesium sulfate. Solvent removal gave (±)-1-(4'-methoxy-phenyl)-3S-azido-4R-[(1S)-carboxyethyl]azetidin-2-one, 7 in 91.5% yield as almost colorless solid.

NMR(D$_6$-Acetone): 1.22(d, J=7 Hz, CH$_3$) 3.38-3.52(m, $\overline{CHCH_3}$) 3.82(s, OCH$_3$) 4.86-4.94(dd, J=5, & 7 Hz, $\overline{H4}$) 5.34(d, J=5 Hz, H3) 6.96-7.50(m, phenyl H's)

EXAMPLE 8

(±)-1-(4'-Methoxyphenyl)-3S-Azido-4R-[(1R)-CarboxyEthyl]azetidin-2-one, 7a

Similar oxidation of (±)-1-(4'-methoxyphenyl)-3S-azido-4R-[(1R)-carboxaldehydoethyl]azetidin-2-one with Jones Reagent gave (±)-1-(4'-methoxyphenyl)-3S-azido-4R-[(1R)-carboxyethyl]azetidin-2-one, 7a, in 90% yield as almost colorless solid.

NMR(D$_6$-Acetone): 1.24(d, J=7 Hz, CH$_3$) 2.9-3.1(m, $\overline{CHCH_3}$) 3.80(s, OCH$_3$) 4.88-4.96(dd, J=5 & 7 Hz, H4) $\overline{5.31}$(d, J=5 Hz, H3) 6.84-7.46(phenyl H's)

IR(Thin Film): 2128 cm$^{-1}$ (N$_3$) 1756 cm$^{-1}$ (β-Lactam CO) 1724 cm$^{-1}$ (COOH)

EXAMPLE 9

(±)-1-(4-Methoxyphenyl)-3S-azido-4R-[(1S)-MethoxyCarbonylethyl]azetidin-2-one, 8

10 mG of (±)-1-(4'-methoxyphenyl)-3S-azido-4R-[(1S)-carboxyethyl]azetidin-2-one, 7, was dissolved in ethylacetate (2 mL), and a solution of freshly prepared diazomethane in ether was added cautiously until a yellow color persisted. Solvent was then removed in vacuo at room temperature to give (±)-1-(4'-methoxyphenyl)-3S-azido-4R-[(1S)-methoxycarbonyl-ethyl-]azetidin-2-one, 8, as colorless oil (10 mG).

NMR(CDCl$_3$): 1.26(d, J=7 Hz, CH$_3$) 3.1-3.26(m, $\overline{CHCH_3}$) 3.6 & 3.82(2 singlets, OCH$_3$'s) 4.62-4.70(dd, $\overline{J=5}$ & 7 Hz, H4) 5.01(d, J=5.0 Hz, H3) 6.92-7.34(phenyl H's)

EXAMPLE 10

(±)-1-(4'Methoxyphenyl)-3S-Azido-4R-[(1R)-MethoxyCarbonyethyl]azetidin-2-one, 8a Similar treatment of (±)-1-(4'-methoxyphenyl)-3S-azido-4R-[(1R)-Carboxyethyl]azetidin-2-one, 7a, with diazomethane gave (±)-1-(4'-methoxyphenyl)-3S-azido-4R-[(1R)-methoxycarbonylethyl]azetidin-2-one, 8a, as colorless oil.

NMR(CDCl$_3$): 1.25(d, J=7.5 Hz, CH$_3$) 2.84-3.05(m, $\overline{CHCH_3}$) 3.8 & 3.82(2 singlets, OCH$_3$'s) 4.71-4.81(dd, $\overline{J=5.5}$ & 7 Hz, H4) 5.0(d, J=5.5 Hz, H3) 6.9-7.37(phenyl H's)

IR(Thin Film): 2150 cm$^{-1}$ (N$_3$) 1786 cm$^{-1}$ (β-Lactam CO) 1754 cm$^{-1}$ (COOCH$_3$)

EXAMPLE 11

(±)-1-(4'-Methoxyphenyl)-3S-Amino-4R-(1S)-[(4R)-2,2-Dimethyl-1,3-Dioxolanyl)]Ethyl]Azetidin-2-one, 9

To a suspension of (±)-1-(4'-methoxyphenyl)-3S-azido-4R-[(1'S)-[(4R)-2,2-dimethyl-1,3-dioxolanyl)]ethyl]azetidin-2-one, 3, (6.92 G, 20 mM) in ethanol (100 mL) was added 650 mG of platinum oxide. This mixture was shaken under an atmosphere of hydrogen on a Parr shaker at room temperature and 45 psi. After 6 hours, the catalyst was filtered on a bed of celite and washed with 3×15 mL of ethylacetate. The solvent was removed to give 6.20 G (97%) of (±)-1-(4'-methoxyphenyl)-3S-amino-4R-(1'S)-[(4R)-(2,2-dimethyl-1,3-dioxolanyl)]ethyl]azetidin-2-one, 9, as thick oil, which slowly solidified as a waxy solid.

NMR(CDCl$_3$): 1.07(d, J=7 Hz, CH$_3$) 1.26 & 1.46(2 singlets acetonide CH$_3$'s) 3.81(s, OCH$_3$) 4.06-4.16(dd, J=5,9 Hz, H4) 4.46(d, J=5 Hz, H3) 6.86-7.55(phenyl H's)

IR(Thin Film): 3675 cm$^{-1}$ (NH$_2$) 1753 cm$^{-1}$ (β-Lactam C=O)

EXAMPLE 12

(±)-1-(4'-Methoxyphenyl-3S-Amino-4R-(1R)-[(4S)-(2,2-Dimethyl-1,3-Dioxolanyl)]Ethyl azetidin-2-one, 9a Similarly, (±)-1-(4'-methoxyphenyl)-3S-azido-4R-(1'R)-[(4S)-(2,2'-dimethyl-1,3-dioxolanyl)]ethyl azetidin-2-one, 4, was hydrogenated for 8 hours to give 92% of (±)-1-(4'-methoxyphenyl)-3S-amino-4R-[(1'R)-[(4S)-(2,2-dimethyl-1,3-dioxolanyl)]ethyl]azetidin-2-one, 9a, as thick oil, which slowly solidified as waxy solid.

NMR(CDCl$_3$): 1.01(d, J=7 Hz, CH$_3$) 1.37 & 1.45(2 singlets, acetonide CH$_3$'s) 2.3-2.46(m, $\overline{CHCH_3}$) 3.80(s, OCH$_3$) 4.23-4.50(dd, J=5.5 & 7 Hz, $\overline{H4}$) 4.48(d, J=5.5 Hz, H3) 6.90-7.40(phenyl H's)

IR(Thin Film): 1754 cm$^{-1}$ (β-Lactam CO)

EXAMPLE 13

(±)-3S-Amino-4R-[(1S)-4-(2,2-Dimethyl-1,3-Dioxolanyl]Ethyl]Azetidin-2-one, 23

Analogously, (±)-3S-azido-4R-[(1S)-4-(2,2-dimethyl-1,3-dioxolanyl]ethyl]azetidin-2-one, 22, was hydrogenated for 3 hours to afford (±)-3S-amino-4R[(1S)-4-

(2,2-dimethyl-1,3-dioxolanyl]ethyl]azetidin-2-one, 23, as thick oil in quantitative yield.

IR(Thin Film): 3350 cm$^{-1}$ (NH, NH$_2$) 1775 cm$^{-1}$ (β-Lactam CO)

EXAMPLE 14

(±)-3S-Amino-4R-[(1R)-4-(2,2-Dimethyl-1,3-Dioxolanyl]Ethyl]azetidin-2-one, 23a

Similarly, (±)-3S-azido-4R-[(1R)-4-(2,2-dimethyl-1,3-dioxolanyl)]ethyl]azetidin-2-one, 22a, was hydrogenated for 6 hours to give (±)-3S-amino-4R-[(1S)-4-(2,2-dimethyl-1,3-dioxolanyl]ethyl]azetidin-2-one, 23a, as thick oil in quantitative yield.

EXAMPLE 15

(±)-1-(4'-Methoxyphenyl)-3S-Amino-4R-[(2S)-(1-Phenyl-1-Hydroxy)Propyl]Azetidin-2-one, 40 (X=CH)

Analogously, (±)-1-(4'-methoxyphenyl)-3S-azido-4R-[(2S)-(1-phenyl-1-hydroxy)propyl]azetidin-2-one, 39 (X=CH), was hydrogenated for 10 hours to give (±)-1-(4'-methoxyphenyl)-3S-amino-4R-[(2S)-(1-phenyl-1-hydroxy)propyl]azetidin-2-one, 40 (X=CH) in quantitative yield.

NMR(CDCl$_3$): 1.18(d, J=7 Hz, CH$_3$) 2.82-2.96(m, CHCH$_3$) 3.78(s, OCH$_3$) 3.98-4.04(dd, J=5.5 & 3.5 Hz, H4) 4.27(d, J=5.5 Hz, H3) 4.98(d, J=4 Hz, CHO) 6.82-7.44(aromatic H's)

EXAMPLE 16

(±)-1-(4'-Methoxyphenyl)-3S-(N-Phthalimido)-4R-[(1S)-[(4R)-(2,2-Dimethyl-1,3-Dioxolanyl)]Ethyl]azetidin-2-one, 10

A mixture of (±)-1-(4'-methoxyphenyl)-3S-amino-4R-[(1'S)-[(4R)-(2,2-dimethyl-1,3-dioxolanyl)]ethyl]azetidin-2-one, 9, (3.52 G, 11 mM), and N-(diphenylphosphono) phthalimide (4.169 G, 11 mM) in 22 mL anhydrous toluene was heated under reflux for 1 hour. The reaction mixture was cooled to 0° C. The resulting solid was filtered and washed with 3×5 mL of ice cold toluene. The filtrate was concentrated in vacuo at room temperature. The resulting residue was chromatographed on silica gel using 7:3 ether:petroleum ether as solvent to give 3.50 G (70%) of (±)-1-(4'-methoxyphenyl)-3S-(N-phthalimido)-4R-[(1'S)-[(4R)-(2,2-dimethyl-1,3-dioxolanyl)]ethyl]azetidin-2-one, 10, as white solid.

NMR(CDCl$_3$): 0.98(d, J=7 Hz, CH$_3$) 1.25 & 1.43(2 singlets, acetonide CH$_3$'s) 2.46-2.64(m, CHCH$_3$) 3.82(s, OCH$_3$) 4.36-4.46(dd, J=5 & 9 Hz, H4) 5.62(d, J=5 Hz, H3) 6.9-7.6(phenyl H's) 7.76-8.00(phthalimido H's)

EXAMPLE 17

(±)-1-(4'Methoxyphenyl)-3S-(N-Phthalimido-4R-[(1R)-[(4S)-(2,2-Dimethyl-1,3-Dioxolanyl)]Ethyl]azetidin-2-one, 10a Similar treatment of (±)-1-(4'-methoxyphenyl)-3S-amino-4R-[(1'R)-[(4S)-(2,2-dimethyl-1,3-dioxolanyl)]ethyl]azetidin-2-one, 9a, gave 64% of (±)-1-(4'methoxyphenyl)-3S-(N-phthalimido)-4R-[(1'R)-[(4S)-(2,2-dimethyl-1,3-dioxolanyl)]ethyl]azetidin-2-one, 10a, as amorphous powder.

NMR(CDCl$_3$): 0.75(d, J=7 Hz, CH$_3$) 1.08 & 1.31(2 singlets, acetonide CH$_3$'s) 3.84(s, OCH$_3$) 4.32-4.40(dd, J=5 & 10 Hz, H4) 5.57(d, J=5 Hz, H3) 6.94-7.36(phenyl H's) 7.76-7.96(phtalimido H's)

EXAMPLE 18

(±)-1-(4'-Methoxyphenyl)-3S-(N-phthalimido)-4R-[(2S)-(1-phenyl-1-Hydroxy)Propyl]Azetidin-2-one, 41 (X=CH)

Similar treatment of (±)-1-(4'-methoxyphenyl)-3S-amino-4R-[(2S)-(1-phenyl-1-hydroxy)propyl]azetidin-2-one, 40, (X=CH), gave (±)-1-(4'methoxyphenyl)-3S-(N-phthalimido)-4R-[(2S)-(1-phenyl-1-hydroxy)propyl]azetidin-2-one, 41 (X=CH) in 62% yield as fluffy solid.

Similarly, derivative 41 (X=N) was prepared.

NMR(CDCl$_3$): 0.67(d, J=7 Hz, CH$_3$) 2.01(d, J=3.5 Hz, OH) 3.1-3.24(m, CHCH$_3$) 3.82(s, OCH$_3$) 4.44-4.53(dd, J=8 & 3.5 Hz, CHO) 4.67-4.75(dd, 5.5 & 7 Hz, H4) 5.57(d, J=5.5 Hz, H3) 6.85-7.98(aromatic H's)

EXAMPLE 19

(±)-3S-(N-Phthalimido)-4R-[1S-[(4R)-(2,2-Dimethyl-1,3-Dioxolanyl)]Ethyl]azetidin-2-one, 11

A solution of ceric ammonium nitrate (16.44 G, 30 mM) in distilled water (120 mL) was added over 15 minutes to a well stirred solution of (±)-1-(4'-methoxyphenyl)-3S-(N-phthalimido)-4R-[1'S-[(4R)-2,2-dimethyl-1,3-dioxolanyl)]ethyl]azetidin-2-one, 10, (4.50 G, 10 mM) in acetonitrile (100 mL) at 0° C. under nitrogen, This mixture was then stirred well at −5° C. for 25 minutes, diluted with 250 mL of water, and then extracted with 3×50 mL of ethylacetate. The combined ethyl acetate extracts were washed with 2×25 mL of 5% sodium sulfate solution, 25 mL of 10% sodium bicarbonate solution, and finally 25 mL of saturated sodium chloride solution. After drying over anhydrous magnesium sulfate, the solvent was removed in vacuo at room temperature to give an oil, which was chromatographed on silica gel using ether as solvent to give 2.27 G (66%) of (±)-3S-(N-phthalimido)-4R-[1'S)[(4R)-(2,2-dimethyl-1,3-dioxolanyl)]ethyl]azetidin-2-one, 11, as amorphous powder.

NMR(CDCl$_3$): 0.70(d, J=6.5 Hz, CH$_3$) 1.32 & 1.40(2 singlets, acetonide CH$_3$'s) 1.94-2.06(m, CHCH$_3$) 3.84-3.95(dd, J=5 & 11 Hz; H4) 5.44-5.50(dd, J=5 & 1.5 Hz; H3) 7.74-792(phthalimido H's)

MS: m/e 329(M+-CH$_3$)

EXAMPLE 20

(±)-3S(N-Phthalimido)-4R-[(1R)-[(4S)-(2,2-Dimethyl-1,3-Dioxolanyl)]Ethyl]azetidin-2-one, 11a Similar treatment of (±)-1-(4'-methoxyphenyl)-3S-(N-phthalimido)-4R-[(1'R)[(4S)-(2,2-dimethyl-1,3-dioxolanyl)]ethyl]azetidin-2-one, 10a gave 59% of (±)-3S-(N-phthalimido)-4R-(1'R)[(4S)-2,2-dimethyl-1,3-dixolanyl)]ethyl]azetidin-2-one, 11a, as amorphous powder.

NMR(CDCl$_3$): 1.0(d, J=7 Hz, CH$_3$) 1.18 & 1.32 (2 singlets, acetonide CH$_3$'s) 2.02-2.22(m, CHCH$_3$) 3.94-4.05(dd, J=5 & 10 Hz, H4) 5.44-5.50(dd, J=5 & 1.5 Hz, H3) 7.47-7.92(phthalimido H's)

MS: m/e 329(M+-CH$_3$)

EXAMPLE 21

(±)-3S-Azido-4R-[(1s)-[(4R)-2,2-Dimethyl-1,3-Dioxlanyl)Ethyl]Azetidine-2-one, 22

Analogously, treatment of (±)-1-)4'-methoxyphenyl)-3S-azido-4R-[1S-[(4R)-(2,2-dimethyl-1,3-dioxlanyl)]ethyl]azetidin-2-one, 3, with ceric ammonium nitrate in aqueous acetonitrile gave 65% of (±)-3S-azido-4R-[(1S)-[(4R)-(2,2-dimethyl-1,3-dioxolanyl)ethyl]-azetidin-2-one, 22, as semi solid.

NMR(CDCl₃): 0.88 & 0.94(2d, J=7 Hz, CH₃'s) 1.34 & 1.42 (2 singlets, acetonide CH₃'s) 1.92–2.10(CHCH₃) 3.64–3.75(dd, J=5 & 10 Hz, H4) 4.70–4.82(dd, J=5 & 2.5 Hz, H3)

IR(Thin Film): 3225 cm⁻¹ (NH) 2150 cm⁻¹ (N₃) 1785 cm⁻¹ (β-Lactam C=O)

EXAMPLE 22

(±)-3S-(N-phthalimido)-4R-[1S-(1-phenylcarbonyl)ethyl]azetidin-2-one, 43 (X=CH)

Treatment of (±)-1-(4'-methoxyphenyl)-3S-(N-phthalimido)-4R-[1s-(1-phenylcarbonyl)ethyl]azetidin-2-one, 42 (X=CH) with ceric ammonium nitrate in aqueous acetonitrile gave (±)-3S-(N-phthalimido)-4R-[1S-(1-phenylcarbonyl)ethyl]azetidin-2-one, 43 (X=CH) (63% yield).

NMR(CDCl₃): 1.02(d, J=7 Hz, CH₃) 3.8–3.97(m, CHCH₃) 4.22–4.32(dd, J=5 & 10.5 Hz, H4) 5.55–5.61(dd, J=5 & 1.5 Hz, H3) 7.18–8.02(aromatic H's)

Similarly, analog 43 (X=N) was also prepared.

EXAMPLE 23

(±)-3S-(Allyloxycarbonylamido)-4R-[1S-[4-(2,2-Dimethyl-1,3-dioxolanyl)]Ethyl]azetidin-2-one, 24 (R=Allyloxy)

To a stirred solution of (±)-3S-Amino-4R-[(1S)-[4-(2,2-dimethyl-1,3-dioxolanyl)]ethyl]azetidine-2-one 23 (2.82 G, 13 mM) in 100 mL of anhydrous methylene chloride at 0° C. under nitrogen were added first, pyridine (1.2 m, 15 mM), and allylchloroformate (1.6 mL, 15 mM). After 1.5 hours at 0° C., the reaction mixture was diluted with 175 mL of ethyl acetate and washed with 3×50 mL of ice water. After drying over anhydrous magnesium sulfate, the solvent was removed to give the crude product as thick oil. Chromatography on silica gel using 1:4 cyclohexane: ethylacetate mixture as solvent gave (±)-3S-(allyoxycarbonylamido)-4R-[(1S)-[4-(2,2-dimethyl-1,3-dioxolanyl)]ethyl]azetidin-2-one 24, (R=allyloxy) (2.68 G, 70% form azide) as colorless oil, which slowly solidified on standing.

Similarly, the β-methyl isomer 24a (R=allyloxy) was prepared.

EXAMPLE 24

(±)-3S-(Phenoxyacetamido)-4R-[(1S)-[4-(2,2-Dimethyl-1,3-Dioxolanyl)]Ethyl]Azetidin-2-one, 24a (R=Phenoxymethyl)

Similarly, (±)-3S-amino-4R-[(1S)-[4-(2,2-dimethyl-1,3-Dioxolanyl)]ethyl]azetidin-2-one, 23 on treatment with phenoxyacetyl chloride and triethylamine, gave a crude product, which was applied as a solution in chlorform on silica gel column, and eluted with ether to give (±)-3S-(phenoxyacetamido)-4R-[(1S)-[4-(2,2-dimethyl-1,3-dioxolanyl)]ethyl]azetidin-2-one 24a (R=phenoxymethyl) (75%) as solid mixture of diastereomers.

NMR(CDCl₃): 0.67(d, J=7 Hz, CH₃) 1.32 & 1.40(2 singlets, acetonide CH₃'s) 1.56–1.69(m, CHCH₃) 3.72–3.81(dd, J=5.5 & 10 Hz, H4) 4.57(s, CH₂O) 5.4–5.49(m, H3) 6.90–7.40(phenyl H's)

Similarly, the β-methyl isomer 24a (R=phenoxymethyl) was prepared.

EXAMPLE 25

(±)-1-[[(Allyloxy)Carbonyl]Hydroxymethyl]-3S-(N-Phthalimido)-4R-[(1S)-[(4R)-(2,2-Dimethyl-1,3-Dioxolanyl)]Ethyl]azetidin-2-one, 12

To a well stirred suspension of (±)-3S-(N-phthalimido)-4R-[(1'S)-[(4R)-(2,2-dimethyl-1,3-dioxolanyl)]ethyl]azetidin-2-one 11, (1.72 G, 5 mM) in anhydrous methylene chloride (50 mL) were added freshly distilled allylglyoxalate monohydrate *(R. N. Guthikonda, L. D. Cama, M. Quesada, M. F. Woods, T. N. Salzmann, and B. G. Christensen, J. Med. Chem., 1987, 30, 871.), (0.736 G, 5.5 mM), freshly distilled triethylamine (2.1 mL, 15 mM), and 10 G of powdered 4A molecular sieves. The mixture was vigorously stirred under nitrogen for 12 hours. The solids were filtered and washed with 10×10 mL of ethyl acetate. The filtrate was concentrated in vacuo at room temperature to afford an oily residue. This crude product was chromatographed on silica gel using 4:1 ether: petroleum ether as solvent to give (±)-1-[[(allyloxy)carbonyl]hydroxymethyl]-3S-(N-phthalimido)-4R-[(1'S)-[(4R)-(2,2-dimethyl-1,3-dioxolanyl)]ethyl]azetidin-2-one, 12, (1.4 G, 60%) as a foam.

NMR(CDCl₃): 0.71 & 0.93(d, J=7 Hz, CH₃) 1.34–1.42(acetonide CH₃'s) 7.79–7.96(phthalimido H's)

IR(Thin Film): 3400 cm⁻¹ (OH) 1786 & 1726 cm⁻¹ (phthalimido C=O) 1770 cm⁻¹ (β-Lactam C=O) 1725 cm⁻¹ (ester C=O)

EXAMPLE 26

(±)-1-[[(Allyloxy)Carbonyl]Hydroxymethyl]-3S-(N-Phthalimido)-4R[(1'R)-[(4S)-(2,2-dimethyl-1,3-dioxolanyl)]Ethyl]azetidin-2-one, 12a Similar treatment of (±)-3S-(N-phthalimido)-4R-[(1R)-[(4S)-(2,2-dimethyl-1,3-dioxolanyl)]ethyl]azetidin-2-one, 11a, gave 65% of (±)-1-[[(allyloxy)carbonyl]hydroxylmethyl]-3S-(N-phthalimido)-4R-[(1'R)-[(4S)-(2,2-dimethyl-1,3-dioxolanyl)]ethyl]azetidin-2-one, 12a, as foam.

IR(Thin Film): 3400 cm⁻¹ (OH) 1800 & 1739 cm⁻¹ (phthalimido C=O) 1770 cm⁻¹ (β-Lactam C=O)

NMR(CDCL₃): 1.05 & 1.24(2d, J=7 Hz, CH₃'s) 5.42–5.47(2d, J=5.5 Hz, H3) 7.76–7.95(phthalimido H's)

EXAMPLE 27

(±)-1-[[(Allyloxy)Carbonyl]hydroxymethyl]-3S-(Allyloxycarbonylamido)-4R-[(1S)-(4R)-(2,2-Dimethyl-1,3-Dioxolanyl)]Ethyl]azetidin-2-one, 25 (R=Allyloxy)

Analogously, (±)-3S-(allyloxycarbonylamido)-4R[(1s)-[4-(2,2-dimethyl-1,3-dioxolanyl)]ethyl]azetidin-2-one 24 (R=Allyloxy), on treatment with allylglyoxalate, gave (±)-1-[[(allyloxy)carbonyl]hydroxymethyl]-3S-(allyloxycarbonylamido)-4R[(1S)-[(4R)-(2,2-dimethyl-1,3-dioxolanyl)]ethyl]azetidin-2-one, 25 (R=Allyloxy) as thick oil in 71% yield.

NMR (CDCl₃): 0.88 & 0.90 (d, J=7 Hz, CH₃) 1.25, 1.42 & 1.36, 1.44 (acetonide CH₃'s)

IR(Thin Film): 3350 cm⁻¹ (OH) 1780 cm⁻¹ (β-Lactam C=O) 1685 cm⁻¹ (ester C=O's)

Similarly, the β-methyl isomer 25a (R=allyloxy) was prepared.

EXAMPLE 28

(±)-1-[[(Allyloxy)Carbonyl]Hydroxymethyl]-3S-(PhenoxyAcetamido)-4R-[(1S)-4-(2,2-Dimethyl-1,3-Dioxolanyl)]Ethyl]Azetidin-2-one, 25
(R = Phenoxymethyl)

Analogous treatment of (±)-3S-(phenoxyacetamido)-4R[(1S)-[4-(2,2-dimethyl-1,3-dioxolanyl]ethyl]azetidin-2-one, 24 (R=Phenoxymethyl) with allylglyoxalate afforded (±)-1-[[(allyloxy)carbonyl]hydroxymethyl]-3S-(phenoxyacetamido-4R-[(1S)[4-(2,2-dimethyl-1,3-dioxolanyl)]ethyl]azetidin-2-one, 25 (R=Phenoxymethyl) in 55% yield as colorless oil.

Similarly, the β-methyl isomer 25a (R=phenoxymethyl) was prepared.

EXAMPLE 29

(±)-1-[[(Allyloxy)Carbonyl]hydroxymethyl]-3S-(N-Phthalimido)-4R-[1S-(1-phenylcarbonyl)ethyl]azetidin-2-one, 44

Similar treatment of (±)-3S-(N-phthalimido)-4R-[1S-(1-phenylcarbonyl)ethyl]azetidin-2-one, 43, (X=CH) with allyl glyoxalate provided (±)-1-[[(allyloxy)carbonyl]hydroxymethyl]-3S-(N-phthalimido)-4R[1S-(1-phenylcarbonyl)ethyl]azetidin-2-one, 44, (X=CH) as oil in 58% yield.

NMR(CDCl$_3$): 0.96 & 0.98 (2d, J=7 Hz, CH$_3$) 3.5–4.1 (m, CHCH$_3$) 5.63 (dd, J=5.5 & 1.5 Hz, H3) 7.4–8.0 (aromatic H's)

Similarly, the -methyl isomer 44 (X=N) was prepared and analogously the β-methyl isomers 44a (X=CH) and (X=N) were prepared.

EXAMPLE 30

(±)-1-[[(Allyloxy)Carbonyl](Triphenylphosphoranylidene)Methyl]-3S-(N-Phthalimido)-4R-[(1S)-(4R)-(2,2-Dimethyl-1,3-Dioxolanyl)]Ethyl]Azetidin-2-one, 14

To a stirred solution of (±)-1-[[(allyloxy)carbonyl]-hydroxymethyl]-3S-(N-phthalimido)-4R-[(4R)-(2,2-dimethyl-1,3-dioxolanyl]ethyl]azetidin-2-one, 12 (1.386 G, 3 mM) in anhydrous tetrahydrofuran (15 mL) under nitrogen at −40° C. were added anhydrous 2,6-lutidine (1.05 mL, 9 mM), followed by freshly distilled thionyl chloride (0.65 mL, 9 mM). A white precipitate formed. The reaction mixture was stirred as it warmed to −20° C., diluted with 30 mL of anhydrous toluene, and filtered. The solids were washed with 10 mL of toluene. The filtrate was concentrated in vacuo at room temperature to give (±)-1-[[(allyloxy)carbonyl]chloromethyl]-3S-(N-phthalimido)-4R-[(1'S)-[(4R)-2,2-dimethyl-1,3-dioxolanyl)]ethyl]azetidin-2-one 13 as thick oil, which was used without further purification.

NMR(CDCl$_3$): 0.74 (d, J=7 Hz, CH$_3$) 1.32 & 1.38 (2 singlets, Acetonide CH$_3$'s) 1.86–2.08 (m, CHCH$_3$) 5.45–5.50 (d, J=6 Hz, H3) 7.75–7.90 (phthalimido H's)

IR(Thin Film): 1800 & 1724 cm$^{-1}$ (phthalimido C=O) 1786 cm$^{-1}$ (β-Lactam C=O) 1725 cm$^{-1}$ (ester C=O)

EXAMPLE 31

To the above obtained oil were added triphenylphosphine (1.18 G, 4.5 mM) and anhydrous 2,6-lutidine (0.53 mL, 4.5 mM) in anhydrous dimethylformamide (15 mL). The resulting solution was heated under nitrogen at 80° C. for 3 hours. Solvent was removed in vacuo at <30° C. The dark residue was taken up in 50 mL of ethyl acetate and washed with 2×15 mL of water, 15 mL of saturated sodium chloride solution, and dried over anhydrous magnesium sulfate. Solvent was removed in vacuo. The dark residue was purified on silica gel using ether as solvent to give (±)-1-[[(allyloxy)carbonyl](triphenylphosphoranylidene)methyl]-3S-(N-phthalimido)-4R-[(1'S)-[(4R)-(2,2-dimethyl-1,3-dioxolanyl)]ethyl]azetidin-2-one 14 (1.26 G, 60%) as yellow foam.

IR(Thin Film): 1800 & 1724 cm$^{-1}$ (phthalimido C=O) 1770 cm$^{-1}$ (β-Lactam C=O) 1725 cm$^{-1}$ (ester C=O) 1626 cm$^{-1}$ (ylide)

NMR(CDCl$_3$): 0.44–0.55(CH$_3$) 1.37 & 1.56(2 singlets, acetonide CH$_3$'s) 7.42–7.92(aromatic H's)

MS: m/e 703(M$^+$+H) 702(M$^+$) 262(Pφ$_3$)

EXAMPLE 32

(±)-1-[[(Allyloxy)Carbonyl](Triphenylphosphoranylidene)Methyl]-3S-(N-Phthalimido)-4R-[(1R)-[(4S)-(2,2-Dimmethyl-1,3-Dioxolanyl)]Ethyl]Azetidin-2-one, 14a Similar treatment of (±)-1-[[(allyloxy)carbonyl]hydroxymethyl]-3S-(N-phthalimido)-4R-[(1'R)-[(4S)-2,2-dimethyl-1,3-dioxolanyl)]ethyl]azetidin-2-one, 12a, with 2,6-lutidine and thionylchloride in tetrahydrofuran gave (±)-1-[[(allyloxy)carbonyl]chloromethyl]-3S-(N-phthalimido)-4R-[(1'R)-[(4S)-(2,2-dimethyl-1,3-dioxolanyl)]ethyl]azetidin-2-one, 13a, as thick oil.

IR(Thin Film): 1772 & 1724 cm$^{-1}$ (phthalimido C=O) 1752 cm$^{-1}$ (β-Lactam C=O) 1725 cm$^{-1}$ (ester C=O)

NMR(CDCl$_3$): 0.95 & 1.06 (2d, J=Hz, CH$_3$) 7.76 & 7.94(phthalimido H's)

EXAMPLE 32A

This crude product, on analogous treatment with triphenylphosphine and 2,6-lutidine in dimethylformamide, gave 68% yield of (±)-1-[[(allyloxy)carbonyl](triphenylphosphoranylidene)methyl]-3S-(N-phthalimido)-4R-[(1'R)-[(4S)-(2,2-dimethyl-1,3-dioxolanyl)]ethyl]azetidin-2-one, 14a, as yellow foam.

IR(Thin Film): 1786 & 1724 cm$^{-1}$ (phthalimido C=O) 1770 cm$^{-1}$ (β-Lactam C=O) 1724 cm$^{-1}$ (ester C=O) 1626 cm$^{-1}$ (ylide)

MS: m/e 702(M$^+$) 703(M$^+$+H)

EXAMPLE 33

Analogously, (±)-1-[[(Allyloxy)Carbonyl](Triphenylphosphoranylidene)Methyl]-3S-(AllyloxyCarbonylamido)-(4R)[(1S)-[4-(2,2-Dimethyl-1,3-Dioxolanyl)]ethyl]azetidin-2-one, 27 (R=Allyloxy) was obtained in 76% yield as foam from (±)-1-[[(allyloxy)carbonyl]hydroxymethyl]-3S-(allyloxycarbonylamido)-4R-[(1S)-[4-(2,2-dimethyl-1,3-dioxolanyl)]ethyl]azetidin-2-one, 25 (R=Allyloxy).

NMR(CDCl$_3$): 0.64–0.76(2d, CH$_3$) 1.33, 1.40 & 1.44(acetonide CH$_3$'s) 7.46–7.84(aromatic H's)

Similarly, the β-methyl isomer 25a (R=allyloxy) was prepared.

EXAMPLE 34

Similarly, (±)-1-[[(Allyloxy)Carbonyl](Triphenylphosphoranylidene)Methyl]-3S-(Phenoxyacetamido)-4R-[(1S)-[4-(2,2-Dimethyl-1,3-Dioxolanyl)]Ethyl]azetidine-2-one, 27 (R=Phenoxymethyl) was obtained in 71% yield as white foam from (±)-1-[[(allyloxy)carbonyl]hydroxymethyl]-3S-(phenoxyacetamido)-4R-

[(1S)-[4-(2,2-Dimethyl-1,3-dioxolanyl]ethyl]azetidin-2-one.

Similarly, the β-methyl isomer 27a (R=phenoxymethyl) was prepared.

EXAMPLE 35

(±)-1-[[(Allyloxy)Carbonyl](Triphenylphosphoranylidene)Methyl]-3S-(N-Phthalimido)-4R-[1S-(1-Phenylcarbonyl)Ethyl]azetidin-2-one, 46 (X=CH)

Analogously, (±)-1-[[(allyloxy)carbonyl](triphenylphosphoranylidene)methyl]-3S-(N-phthalimido)-4R-[(1S)-(1-phenylcarbonyl)ethyl]azetidin-2-one, 46 (X=CH) was obtained in 69% yield as pale yellow foam, from (±)-1-[[(allyloxy)carbonyl]hydroxymethyl]-3S-(N-phthalimido)-4R-[(1S)-(1-phenylcarbonyl)ethyl]azetidin-2-one, 44 (X=CH), via the chloride 45 (X=CH), IR(Thin Film): 1780 & 1720 cm$^{-1}$ (phthalimido C=O) 1740 cm$^{-1}$ (β-Lactam C=O) 1720 cm$^{-1}$ (ester C=O) 1680 cm$^{-1}$ (ketone C=O) 1620 cm$^{-1}$ (ylide)

Similarly, the α-methyl isomer 46 (X=N) was prepared, as well as the β-methyl isomers 46a (X=CH) and (X=N).

EXAMPLE 36

(±)-1-[[(Allyloxy)carbonyl](Triphenylphosphoranylidene)Methyl]-3S-(N-Phthalimido)-4R-[3S-(1,2-Dihydroxybutyl)]Azetidin-2-one, 15

Foamy (±)-1-[[Allyloxy)carbonyl](Triphenylphosphoranylidene)Methyl]-3S-(N-Phthalimido)-4R[(1'S)]-(4R)-(2,2-Dimethyl-1,3Dioxolanyl)ethyl]azetidin-2-one 14 (1.0G, 1.425 mM) was added to a stirred mixture of 10 mL of 9:1 trifluoroacetic acid-water at −20° C. The reaction mixture was stirred for 0.5 hour while the resulting solution warmed to 0° C. This mixture was then cautiously neutralized and extracted with 3×15 mL of ethyl acetate. The combined organic extracts were then washed with 2×15 mL of saturated sodium bicarbonate solution, 15 mL of saturated sodium chloride solution, and dried over anhydrous magnesium sulfate. Solvent removal gave (±)-1-[[(Allyloxy)Carbonyl](Triphenylphosphoranylidene)methyl]-3S-(N-Phthalimido)-(4R)-[3S-(1,2-Dihydroxybutyl)]azetidin-2-one 15 (805 mG, 85%) as pale yellow amorphous solid.

IR(Thin Film): 3400 cm$^{-1}$ (OH) 1786 & 1724 cm$^{-1}$ (Phthalimido C=O) 1777 cm$^{-1}$ (β-Lactam C=O) 1740 cm$^{-1}$ (Ester C=O) 1613 cm$^{-1}$ (Ylide).

NMR (CDCl$_3$): 0.46, (CH$_3$) 7.5–7.9(Aromatic H's).
MS: m/e 663(M$^+$ +H) 262(Pφ$_3$)

EXAMPLE 37

Analogous Treatment gave (±)-1-[[(Allyloxy)carbonyl](Triphenylphosphoranylidene)methyl]-3S-(N-Phthalimido)4R-[(3R)-(1,2-Dihydroxybutyl)]azetidin-2-one, 15a; in 93% yield as pale yellow amorphous solid from (±)-1-[[(allyloxy)carbonyl](Triphenylphosphoranylidene)methyl]-(3S)-(N-Phthalimido)-4R-[(1'R)-[(4S)-(2,2-dimethyl-1,3-dioxolanyl)]ethyl]azetidin-2-one, 14a.

IR(Thin Film): 3400 cm$^{-1}$ (OH) 1786 & 1724 cm$^{-1}$ (Phthalimido C=O) 1754 cm$^{-1}$ (β-Lactam C=O) 1725 cm$^{-1}$ (Ester C=O) 1618 cm$^{-1}$ (Ylide).

NMR(CDCl$_3$): 0.93(d, J=7 Hz, CH$_3$) 7.25-7.9(Aromatic H's).
MS: m/e 663(M$^+$ +H)

EXAMPLE 38

(±)-1-[[(Allyloxy)carbonyl](Triphenylphosphoranylidene)Methyl]-3S-(Allyloxycarbonylamido)-4R-[(3S)-(1,2-Dihydroxybutyl)]azetidin-2-one, 28 (R=allyloxy)

Similarly, (±)-1-[[(Allyloxy)carbonyl](triphenylphosphoranylidene)methyl]-3S-(allyloxycarbonylamido)-4R-[(1S)-]4-(2,2-dimethyl-1,3-dioxolanyl)]ethyl]azetidin-2-one, 27 (R=allyloxy) gave (±)-1-]](allyloxy)carbonyl) (triphenylphosphoranylidene)methyl]-3S-(Allyloxy-carbonylamido)-4R]-(3S)-(1,2-dihydroxybutyl)]azetidin-2-one, 28, (R=Allyloxy) in 75% yield as white foam.

NMR(CDCl$_3$): 0.60–0.90(CH$_3$) 7.44–7.86(Aromatic H's)

Similarly, the β-methyl isomer 28a (R=allyloxy) was prepared.

EXAMPLE 39

Analogously, (±)-1-1]](allyloxy)carbonyl](triphenylphosphoranylidene)methyl]-3S-(Phenoxyacetamido)-4R-[(3S)-(1,2-dihydroxybutyl)]azetidin-2-one, 28, (R=Phenoxymethyl), was obtained as white solid in 85% yield after chromatography on silica gel using ethyl acetate as solvent from (±)-1-[[(allyloxy)carbonyl](Triphenylphosphoranylidene)methyl]-3S-(Phenoxyacetamido)-4R-[(1S)-[4-(2,2-dimethyl-1,3-dioxolanyl]ethyl]azetidin-2-one 27 (R=Phenoxymethyl).

Similarly, the β-methyl isomer 28a (R=phenoxymethyl) was prepared.

EXAMPLE 40

(±)Allyl-(1R,5R,6S)-6-(N-Phthalimido)-1-methylcarbapen-2-em-3-carboxylate, 16

Periodic acid (228 mG, 1 mM) was added to a stirred solution of (±)-1-[[allyloxy)-carbonyl](Triphenyl-phosphoranylidene)Methyl]-3S-(N-Phthalimido)-4R-[3S-(1,2-Dihydroxybutyl]azetidin-2-one 15 (331 mG, 0.5 mM), in 10 mL of tetrahydrofuran. A white precipitate separated out. After stirring for 15 minutes under nitrogen, the reaction mixture was diluted with 20 mL of ethyl acetate, and washed with 2×25 mL of saturated sodium bicarbonate, 25 mL of saturated sodium chloride solution, and dried over anhydrous magnesium sulfate. Solvent was removed in vacuo at room temperature. The residual solid was chromatographed on silica gel using ether as solvent, to give (±)allyl-(1R,5R,6S)-6-(N-Phthalimido)-1-methylcarbapen-2-em-3-carboxylate, 16 (77%) as white solid melting at 181°-2° C.

NMR(CDCl$_3$): 1.21(d, J=7 Hz, CH$_3$); 3.29–3.46(m, H1) 4.11–4.20(dd, J-6 & 8 Hz, H5) 4.70–4.91, 5.27–5.53 & 5.91–6.13(m, CH$_2$—CH=CH$_2$) 5.83(d, J=6 Hz, H6) 6.58(d, J=2.5 Hz, H2) 7.79–7.97(m, Phthalimido).

IR(Thin Film): 1800 & 1724 cm$^{-1}$(Phthalimido C=O) 1780 cm$^{-1}$(β-Lactam C=O) 1725 cm$^{-1}$(ester C=O)

MS: m/e 352(M$^+$) Calculated for C$_{19}$H$_{16}$N$_2$O$_5$: =352.1059 Found=352.1059

EXAMPLE 41

Preparation of
(±)-[[(Allyloxy)carbonyl](Triphenylphosphoranylidene)methyl]-3S-(N-Phthalimido)-4R-[(1R)-(1-carboxaldehydo)Ethyl]azetidin-2-one (15a)

Periodic acid (365 mG, 1.6 mM) was added to a stirred suspension of (±)-[[(allyloxy)carbonyl](triphenylphosphoranylidene)methyl]-3S-(N-Phthalimido)-4R-[(3R)-(1,2-Dihydroxybutyl)]azetidin-2-one (530 mG, 0.8 mM) in 10 mL of anhydrous tetrahydrofuran under nitrogen. Within 2-3 minutes, the suspension went into solution and the reaction mixture remained homogeneous briefly. With 2 minutes thereafter, a solid started precipitating out. The reaction mixture was stirred for 15 minutes total from the start of the reaction. It was then diluted with 30 mL of ethyl acetate, and washed with 2×25 mL of saturated sodium chloride solution. After drying the organic phase over anhydrous magnesium sulfate, the solvent was removed in vacuo at room temperature to yield (±)-[[(allyloxy)-carbonyl](Triphenylphosphoranylidene)methyl]-3S-(N-Phthalimido)-4R-[(1R)-(1-carboxaldehydo)Ethyl]-]azetidin-2-one 15a (500 mG, 90%) as solid, which was further used without purification.

NMR(CDCl$_3$): 1.43(d, J=7 Hz, CH$_3$) 9.35(d, J=1 Hz, CHO).

IR(Thin Film): 1786 & 1724 cm$^{-1}$(Phthalimido C=O) 1770 cm$^{-1}$($\beta$-Lactam C=O) 1725 cm$^{-1}$(Ester C=O & Aldehyde C=O) 1626 cm$^{-1}$(Ylide)

MS: m/e 630(M+) 631(M+ +H)

EXAMPLE 42

Allyl(±)-(1S,5R,6S)-6-(N-Phthalimido)-1-Methylcarbapen-2-em-3-Carboxylate, 16a

A solution of 250 mG (0.4 mM) of (±)-1-[[(Allyloxy)-carbonyl](Triphenylphosphoranylidene)methyl]-3S-(N-Phthalimido)-4R-[(1R)-(1-Carboxaldehydro)ethyl-]azetidin-2-one, 15a, in 10 mL of anhydrous toluene was heated to reflux for 1.75 hours. The solvent was then removed in vacuo at room temperature. The resulting residue was purified on silica gel using ether as solvent, to provide (±)allyl-(1S,5R,6S)-6-(N-Phthalimido)-1-Methylcarbapen-2-em-3-carboxylate, 16a (72%) as white solid melting at 137°-8° C.

NMR(CDCl$_3$): 1.08(d, J=7.5 Hz, CH$_3$); 3.34-3.56(m, H1) 4.58-4.68(dd, J=6 & 11.5 Hz, H5) 4.68-4.90, 5.24-5.54 & 5.90-6.10(m, CH$_2$—CH=CH$_2$) 5.78(d, J=6 Hz, H6); 6.43(d, J=3 Hz, H2) 7.78-7.96(m, Phthalimido)

IR(Thin Film): 1800 & 1724 cm$^{-1}$(Phthalimido) 1786 cm$^{-1}$($\beta$-Lactam C=O) 1725 cm$^{-1}$(ester C=O)

MS: m/e 352 (M+) Calculated for C$_{19}$H$_{16}$N$_2$O$_5$=352.1059 Found:=352.1059

EXAMPLE 43

(±)Allyl-(1S,5R,6S)-6-[Allyloxycarbonylamido)-1-Methylcarbapen-2-em-3-carboxylate, 29 (R=Allyloxy)

To a stirred solution of (±)-1-[[(Allyloxy)carbonyl]-(Triphenylphosphoranylidene)Methyl]-3S-(Allyloxycarbonylamido)-4R-[(3S)-(1,2-Dihydroxybutyl)]azetidin-2-one, 28 (R=Allyloxy) (30.8 mG, 0.05 mM) in anhydrous methylene chloride, (1 mL) tetrahydrofuran (0.4 mL) mixture under nitrogen were added first 2,6-lutidine (6 ml, 0.05 mM) and then periodic acid (11.5 mG, 0.05 mM). The mixture was then heated in an oil bath at 45°-47° C. for 15 minutes, cooled to room temperature, diluted with 5 mL of ethyl acetate, and washed with 2×2 mL of pH 7 phosphate buffer solution, 4 mL of saturated sodium chloride solution. The organic layer was dried over anhydrous magnesium sulfate. Solvent was removed in vacuo at room temperature to give 32 mG of the crude product, whose NMR spectrum showed the presence of only the desired carbapenem along with triphenyl phosphine oxide, and some 2,6-lutidine.

This crude product was purified on silica gel using 1:1 ether:petroleum ether as solvent to give 10 mG of (±)allyl-(1S,5R,6S)-6-[allyloxycarbonylamido)-1-methylcarbapen-2-em-3-carboxylate, 29 (R=allyloxy) as oil.

NMR(CDCl$_3$): 1.27(d, J=8 Hz, CH$_3$) 3.15-3.35(m, CHCH$_3$) 4.0-4.11(dd, J=5.5 & 8.5 Hz, H5) 6.56(d, J=2.5 Hz, H2)

IR(Thin Film): 3320 cm$^{-1}$ (NH) 1795 cm$^{-1}$ ($\beta$-Lactam C=O) 1725 cm$^{-1}$ (Ester C=O)

Similarly, the $\beta$-methyl isomer 29a (R=allyloxy) was prepared.

EXAMPLE 44

(±)Allyl-(1R,5b,6S)-6-(Phenoxyacetamido)-1-Methylcarbapen-2-em-3-carboxylate, 29 (R=Phenoxymethyl)

Analogously, (±)-1-[[(Allyloxy)carbonyl]-(Triphenylphosphoranylidene)methyl]-3S-(Phenoxyacetamido)-4R-[(3S)-(1,2-Dihydroxybutyl)]azetidin-2-one, 28 (R=Phenoxymethyl) gave allyl (±)-(1R,5R,6S)-6-(Phenoxyacetamido)-1-Methylcarbapen-2-em-3-carboxylate, 29 (R=Phenoxymethyl) as crude product, contaminated with triphenylphosphine oxide and some 2,6-lutidine, (almost quantitative yield) as oil. This crude product was used directly in the next reaction without further purification. This crude could be stored overnight at −78° without decomposition. Also, flash column chromatography on silica gel using 7:3 ether:petroleum ether as solvent led to extensive decomposition of the carbapenem and gave 22% of the desired carbapenem as oil.

NMR(CDCl$_3$): 1.22(d, J=7 Hz, CH$_3$) 2.91-3.10(m, CHCH$_3$) 4.05-4.14(dd, J=5.5 & 9 Hz, H5) 4.57(s, CH$_2$O) 5.38-5.47(dd, J=5.5 & 6 Hz, H6) 6.48(d, J=2 Hz, H2)

IR(Thin Film): 3200 cm$^{-1}$ (NH) 1776 cm$^{-1}$ ($\beta$-Lactam C=O) 1724 cm$^{-1}$ (Ester C=O) 1681 cm$^{-1}$ (Amide C=O)

UV: $\lambda$max$^{dioxane}$ 260, 266 & 272 nm

Similarly, the $\beta$-methyl isomer 29a (R=phenoxymethyl) was prepared.

EXAMPLE 45

(±)Potassium-(1R,5R,6S)-6-(N-Phthalimido)-1-methylcarbapen-2-em-3-carboxylate, 17

To a stirred solution of (±)Allyl-(1R,5R,6S)-6-(N-Phthalimido)-1-Methylcarbapen-2-em-3-carboxylate, 16 (70.4 mG, 0.2 mM) in 1:1 methylene Chloride:ethyl acetate (5 mL) were added triphenylphosphine (4 mG), potassium 2-ethyl hexanoate (400 mL of 0.5M solution in ethyl acetate) and then tetrakis (triphenyl phosphine) palladium (6 mG). After 15 minutes under nitrogen, solid started separating out. After 45 mins, the reaction mixture was diluted with 8 mL of ether and centrifuged. The supernatant liquid was removed. The solid was washed with 2×10 mL of ethyl acetate, centrifuged. This solid was suspended in 2 mL of water and applied on 2×500$\mu$ Reverse phase silica gel plates and eluted with 8% ethanol in water. UV active band was scraped, stirred with 40% acetonitrile in water, and filtered. The filtrate was washed with 4×10 mL of hexane. The resulting aqueous phase was concentrated and freeze dried to provide (±)potassium-(1R,5R,6S)-6-(N-Phthalimido)-1-Methyl-carbapen-2-em-3-carboxylate 17 (30 mG, 44%).

NMR(D₂O): 1.15(d, J=7 Hz, CH₃); 3.2-3.4(m, H1); 4.22(dd, J=6 & 7.5 Hz, H5); 5.9(d, J=6 Hz, H6); 6.32(d, J=2.5 Hz, H2) 7.88-8.00(m, Phthalimido).

UV: $\lambda_{max}^{H2O}$ 279 nm & 263 nm

EXAMPLE 46

(±)Potassium-(1S,5R,6S)-6-(N-Phthalimido)-1-Methyl-carbapen-2-em-3-carboxylate, 17a Analogous treatment of (±)Allyl-(1S,5R,6S)-6-(N-Phthalimido)-1-Methylcarbapen-2-em-3-Carboxylate, 16a, gave 52% of (±)potassium-(1S,5R,6S)-6-(N-Phthalimido)-1-Methylcarbapen-2-em-3-carboxylate, 17a.

NMR(D₂O): 0.98(d, J=7.5 Hz CH₃); 3.36-3.56(m, H₁); 4.66(dd, J=& 6 Hz 5.5); 5.67(d, J=5.5 Hz, H6); 6.14(d, J=2.5 Hz; H₂): 7.9-8.0(m, Phthalimido).

UV: $\lambda_{max}^{H2O}$ 303 nm, 263 nm

EXAMPLE 47

(±)Potassium-(1R,5R,6S)-6-(Phenoxyacetamido)-1-Methylcarbapen-2-em-3-Carboxylate, 30 (R=Phenoxymethyl)

To a stirred solution of crude allyl (±)-(1R,5R,6S)-6-(Phenoxyacetamido)-1-Methylcarbapen-2-em-3-carboxylate 29 (R=Phenoxymethyl) (from 166 mG, 0.25 mM of ylide diol) in 5 mL of 1:1 mixture of methylene chloride:ethyl acetate at 0° under nitrogen were added pH 7 "MOPS" Buffer (10 mL of 0.1 Molar solution), triphenylphosphine (10 mG, 0.038 mM), tetrakis (triphenylphosphine)palladium (30 mG, 0.038 mM), and potassium 2-ethyl hexanoate (450 μL of 0.5 Molar solution in ethyl acetate, 0.225 mM) in that order. This two phase system was stirred at 0° for 45 minutes. The organic phase was decanted. The aqueous layer was washed with 3×5 mL of ice cold ethyl acetate and then with 2×5 mL of ice cold ether. The aqueous solution was pumped in vacuo at 0° for 10 minutes.

NMR spectrum was obtained by using D₂O solutions of the above mentioned aqueous solutions. U.V. and NMR spectra indicated efficiently deblocked product. U.V. yield of this product was 27 mG/10 mL of solution. Yield of some samples varied from 10-20 mG/10 mL.

NMR (0.1M pH7 "MOPS" or phosphate buffer): 1.07(d, J=7 Hz, CH₃) 2.90-3.10(m, CHCH₃) 4.0-4.09(dd, J=5.5 & 8.5 Hz, H5) 5.46(d, J=5.5 Hz, H6) 6.24(d, J=2 Hz, H2) 6.96-7.8(Aromatic H's) 0.1M pH7 phosphate or "MOPS" buffer UV: $\lambda_{max}$ 262, 267, 273 nm Similarly, the β-methyl isomer 30a (R=phenoxymethyl) was prepared.

EXAMPLE 48

(±)-1-[[(Allyloxy)Carbonyl](Triphebylphosphoranylidene)Methyl]-3(S)-(N-Phthalimido)-4R-[3(S)-1-Acetocy-2-Hydroxy)Butyl]Azetidin-2-one, 18 (X=OAc)

To a stirred solution of (±)-1-[[(allyloxy)carbonyl](-triphenylphosphoranylidene)methyl]-3(S)-(N-Phthalimido)-(4R)-[3(S)-(1,2-Dihydroxybutyl)]azetidin-2-one, 15, (267 mG, 0.4 mM) in 8 mL of anhydrous methylene chloride under nitrogen at room temperature were added 4-N,N-dimethylaminopyridine (136 mG, 1.2 mM) and acetyl chloride (92 μL. 1.2 mM). This mixture was stirred for 3 hours, diluted with 20 mL of ethyl acetate and washed with 3×5 mL of water, 5 mL of saturated sodium bicarbonate solution. The organic layer was dried over anhydrous magnesium sulfate. Solvent removal afforded 280 mG (99%) of (±)-1-[[(allyloxy)carbonyl](triphenylphosphoranylidene)methyl]-3S-(N-phthalimido)-(4R)-[3S-(1-acetoxy, 2-hydroxy)-butyl]azetidin-2-one, 18 (X=OAc), as yellow foam. This crude product was used in the next reaction without further purification.

NMR(CDCl₃): 0.45-0.56(2d, J=7 Hz, CH₃) 2.04 & 2.11(2s, Acetate CH₃) 7.44-7.88(Aromatic H's)

IR(Thin Film): 3600 cm⁻¹ (OH) 1800 & 1724 cm⁻¹ (Phthalimido C=O) 1770 cm⁻¹ (β-Lactam C=O) 1754 & 1725 cm⁻¹ (Ester C=O's) 1626 cm⁻¹ (Ylide)

Similarly, the β-methyl isomer 18a (X=OAc) was prepared.

EXAMPLE 49

(±)-1-[[(Allyloxy)Carbonyl](Triphenylphosphoranylidene)Methyl]-3S-(N-Phthalimido)-(4R)-[3S-[1-(t-ButylDimethylSilyl)oxyl-2-Hydroxybutyl]Azetidin-2-one, 18 (R=OSiMe₂CMe₃)

To a stirred solution of (±)-1-[[(allyloxy)carbonyl](-triphenylphosphoranylidene)methyl]-3(S)-(N-phthalimido)-(4R)-[3(S)-(1,2-dihydroxybutyl)]azetidin-2-one, 15, (200 mG, 0.3 mM) in 6 mL of anhydrous methylene chloride under nitrogen at room temperature were added 4-N,N-dimethylaminopyridine (110 mG, 0.9 mM) and t-butyldimethylsilylchloride (136 mG, 0.9 mM). The reaction mixture was stirred under nitrogen for 12 hours, diluted with 15 mL of ethyl acetate, and washed with 2×5 mL ice water, 5 mL of ice cold 1 Normal hydrochloric acid, and 5 mL of saturated sodium bicarbonate solution. After drying over anhydrous magnesium sulfate, the solvent was removed to give (±)-1-[[(allyloxy)carbonyl](triphenylphosphoranylidene)methyl]-3(S)-(N-phthalimido)-(4R)-[3(S)-[1-(t-butyldimethylsilyl)oxy]-2-hydroxybutyl-]azetidin-2-one, 18 (R=OSiMe₂CMe₃), (250 mG) as white foam. This material was used in the next reaction without further purification.

Similarly, the β-methyl isomer 18a (X=OSiMe₂CMe₃) was prepared.

EXAMPLE 50

(±)-1-[[(Allyloxy)Carbonyl](Triphenylphosphoranylidene)Methyl]-3S-(N-Phthalimido)-[(3S)-(1-Acetoxy-2-Keto)Butyl]Azetidin-2-one, 19 (X=OAc)

To a stirred solution of (±)-1-[[(allyloxy)carbonyl](-triphenylphosphoranylidene)methyl]-3S-(N-phthalimido)-(4R)-[3S-(1-acetoxy-2-hydroxy)butyl-]azetidin-2-one, 18 (X=OAc), (275 mG, ~0.4 mM) in 14 mL of acetone was added 4 molar Jones Reagent (300 μL, 1.2 mM). The reaction mixture was stirred for 3 hours. A gummy green solid coated the surface. Solvent was then removed in vacuo at room temperature. The residue was shaken with 12 mL of ethyl acetate and 8 mL of water and then with 8 mL of saturated sodium bicarbonate. The organic phase was dried over anhydrous magnesium sulfate. Solvent removal in vacuo at room temperature afforded (±)-1-[[(allyloxy)carbonyl](triphenylphosphoranylidene)methyl]-3S-(N- phthalimido-(4R)-[3S-(1-acetoxy-2-keto)butyl]azetidin-2-one, 19 9(X=OAc), (275 mG of crude product) as light yellow foam. This material was used with out further purification.

NMR(CDCl₃): 0.74(d, J=7 Hz, CH₃) 1.21 & 1.23(2s, Acetate CH₃'s) 4.86–5.20(CH₂ OAC) 7.46–7.90(Aromatic H's)

IR(Thin Film): 1800 & 1724 cm⁻¹ (Phthalimido C=O) 1770 cm⁻¹ (β-Lactam C=O) 1754 & 1725 cm⁻¹ (Ester & Ketone C=O's) 1653 cm⁻¹ (Ylide)

Similarly, the β-methyl isomer 19a (X=OAc) was prepared.

EXAMPLE 51

(±)-1-[[(Allyloxy)Carbonyl](Triphenylphosphoranylidene)Methyl]-3S-(N-Phthalimido)-(4R)-[3S-(1-t-Butyldimethyl-Silyloxy-2-Hydroxy)Butyl]Azetidin-2-one, 19 (X=OSiMe₂CMe₃)

Analogously, (±)-1-[[(allyloxy)carbonyl](triphenylphosphoranylidene)methyl]-3S-(N-phthalimido)=(4R)-[3S-(1-t-butyldimethylsilyloxy-2-keto)butyl]-azetidin-2-one, 18, (X=OSiMe₂CMe₃) was obtained in 70% yield from the oxidation of (±)-1-[[(allyloxy)carbonyl](triphenylphosphoranylidene)methyl]-3S-(N-Phthalimido)-(4R)-[3S-(1-t-butylidimethylsilyloxy-2-hydroxy)butyl]azetidin-2-one, 19 (X=OSiMe₂CMe₃) with Jones Reagent.

NMR(CDCl₃): 0.02–0.16 & 0.87 & 0.90(Si CH₃'s) 0.63–0.72(CH₃) 7.44–7.86(Aromatic H's)

IR(Thin Film): 1800 & 1729 cm⁻¹ (Phthalimido C=O) 1770 cm⁻¹ (β-Lactam C=O) 1725 cm⁻¹ (Ester C=O) 1660 cm⁻¹ (Ylide)

Similarly, the β-methyl isomer 19a (X=OSiME₂CMe₃) was prepared.

EXAMPLE 52

(±)-1-(4'Methoxyphenyl)-3S-)N-Phthalimido)-4R-[1S-(1-Phenylcarbonyl)Ethyl]Azetidin-2-one, 42

Similar treatment of (±)-1-(4'-methoxyphenyl)-3S-(N-phthalimido)-4R-[(2S)-(1-phenyl-1-hydroxy)propyl]azetidin-2-one, 41 (X=CH), gave (±)-1-)4'methoxyphenyl)-3S-(N-phthalimido)-4R-[1S-(1-Phenylcarbonyl)ethyl]azetidin-2-one, 42 (X=CH) in 85% yield.

NMR(CDCl₃): 1.04(d, J=7 Hz, CH₃) 3.66(s, OCH₃) 4.0–4.18(m, CHCH₃) 4.72–4.82(dd, J=5 & 10.5 Hz, H4) 5.72(d, J=5 Hz, H3) 6.56–8.04(Aromatic H's)

Similarly, the β-methyl isomer 42a (X=CH) was prepared.

EXAMPLE 53

(±)-1-[[(Allyloxy)Carbonyl](Triphenylphosphoranylidene)Methyl]-3S-(N-Phthalimido)-(4R)-[(3S)-(1-Hydroxy-2-keto)Butyl]azetidin-2-one, 19 (X=OH)

To a stirred solution of (±)-1-[[(allyloxy)carbonyl](-triphenylphosphoranylidene)methyl]-3S-(N-phthalimido)-azetidin-2-one, 19 (X=OSiMe₂CMe₃), (68 mG, 0.087 mM) in 2 mL anhydrous tetrahydrofuran at room temperature under nitrogen were added acetic acid (105 μL, 1.84 mM) first followed by n-tetrabutyl ammonium fluoride (600 μL of 1 molar solution in THF, 0.6 mM). After 5 hours, the reaction mixture was diluted with 5 mL of ethyl acetate and washed with 2×2 mL of water, 2 mL of saturated sodium bicarbonate solution, and 2 mL of saturated sodium chloride solution. The organic phase was dried over anhydrous magnesium sulfate. Solvent was removed to give the product as foam, which was chromatographed on silica gel using 1:1 ether:ethylacetate as solvent to afford 86% of (±)-1-[[(allyloxy)carbonyl](triphenylphosphoranylid-ene)methyl]-3S-(N-phthalimido)-(4R)-[(3S)-(1-hydroxy-2-keto)butyl]azetidin-2-one, (19) (X=OH) as white foam.

NMR(CDCl₃): 0.68 & 0.96(2d, J=7 Hz, CH₃'s) 3.36–3.48(dd, J=5.5 & 12 Hz, H4) 7.42–7.88(Aromatic H's)

IR(Thin Film): 3600 cm⁻¹ (OH) 1800 & 1724 cm⁻¹ (Phthalimido CO's) 1770 cm⁻¹ (β-Lactam C=O) 1754 & 1725 (Ester & Ketone C=O's) 1626 cm⁻¹ (Ylide)

Similarly, the β-methyl isomer 19a (X=OH) was prepared.

EXAMPLE 54

(±)Allyl-(1R,5R,6S)-2-Acetoxymethyl-6-(N-Phthalimido)-1-MethylCarbapen-2-em-3-Carboxylate, 20, (X=OAc)

A solution of (±)-1-[[(allyloxy)carbonyl](triphenylphosphoranylidene)methyl]-3S-(N-phthalimido)-(4R)-[(3S)-(1-acetoxy-2-keto)butyl]azetidin-2-one, (19, X=OAc) (70.8 mG, 0.1 mM) in 5 mL of anhydrous toluene was heated under nitrogen in an oil bath at 110° for 20 minutes. The solvent was removed in vacuo at room temperature to afford an oil. This residue was chromatographed on silica gel using ether as solvent to give 30 mG (70%) of (±)allyl-(1R,5R,6S)-2-acetoxymethyl-6-(N-phthalimido)-1-methylcarbapen-2-em-3-carboxylate, (20) (X=OAc); as a white solid melting at 107°–8° C.

NMR(CDCl₃): 1.22(d, J=7 Hz, CH₃) 2.09(s, Acetate CH₃) 3.3–3.49(m, CHCH₃) 4.02–4.10(dd, J=5.75 & 8 Hz, H5) 5.05–5.30(CH₂OAC) 5.78(d, J=5.75 Hz, H6) 7.74–7.90(Phthalimido H's)

IR(Thin Film): 1820 & 1720 cm⁻¹ (Phthalimido C=O) 1780 (β-Lactam C=O) 1750 & 1715 (Ester C=O)

Similarly, the β-methyl isomer 20a (X=OAc) was prepared.

EXAMPLE 55

(±)Allyl-(1R,5R,5S)-2-(t-Butyldimethylsilyloxymethyl)-6-(N-Phthalimido)-1-Methylcarbapen-2-em-3-Carboxylate, 20 (X=OSiMe₂CMe₃)

Analogously, cyclization of (±)-1-[[(allyloxy)carbonyl](triphenylphosphoranylidene)methyl]-3S-(N-phthalimido)-(4R)-[(3S)-(1-t-butyldimethylsilyloxy-2-keto)butyl]azetidin-2-one, 19 (X=OSiMe₂CMe₃) in toluene at 110° for 45 minutes gave 20% yield of allyl (±)-(1R,5R,6S)-2-(t-butyldimethylsilyloxymethyl)-6-(N-phthalimido)-1-methyl-carbapen-2-em-3-carboxylate 20 (X=OSiMe₂CMe₃) as an oil.

NMR(CDCl₃): 3.98–4.06(dd, J=5.5 & 8 Hz, H5) 5.76(d, J=5.5 Hz, H6) 7.73–7.92(Phthalimido H's)

Similarly, the β-methyl isomer 20a (X=OSiMe₂CMe₃) was prepared.

EXAMPLE 56

Similarly, (±)Allyl-(1R,5R,6S)-2-(Hydroxymethyl)-6-(N-Phthalimido)-1-Methylcarbapen-2-em-3-carboxylate, (20, X=OH) melting at 160°, was obtained in 88% yield by heating (±)-1-[[(allyloxy)carbonyl](triphenylphosphoranylidene)methyl]-3S-(N-phthalimido)-(4R)-[(3S)-(1-hydroxy-2-keto)butyl]azetidin-2-one, (19) (X=OH) in toluene at 110° for 11 minutes.

NMR(CDCl₃); 1.22(d, J=7.5 Hz, CH₃) 3.03–3.13(dd, J=5.5 & 8.5 Hz, OH) 3.33–3.53(m, CHCH₃)

4.02–4.11(dd, J=5.5 & 8 Hz, H5) 4.24–4.76(m, CH$_2$OH) 5.77(d, J=5.5 Hz, H6) 7.72–7.89(m, Phthalimido H's)

IR(Thin Film); 3675 cm$^{-1}$ (OH) 1820 & 1736 cm$^{-1}$ (Phthalimido C=O) 1770 cm$^{-1}$ (β-Lactam C=O) 1725 (Ester C=O)

Similarly, the β-methyl isomer 20a (X=OH) was prepared.

EXAMPLE 57

Similarly, (±)Allyl-(1R,5R,6S)-2-Phenyl-6-(N-Phthalimido-1-methylcarbapen-2-em-3-Carboxylate, 47 (X=CH) was obtained by heating (±)-1-[[(allyloxy)-carbonyl](triphenylphosphoranylidene)methyl-3S-(N-phthalimido)-4R-[(1S)-(1-phenylcarbonyl)ethyl]azetidin-2-one, 46 (X=CH).

NMR(CDCl$_3$): 1.02(d, J=7 Hz, CH$_3$) 3.60–3.77(m, H1) 4.18–4.25(dd, J=5.5 & 8 Hz, H5) 5.86(d, J=5.5 Hz, H6) 7.2–7.4(Phenyl H's) 7.76–7.98(Phthalimido H's)

IR(Thin Film): 1800 & 1725 cm$^{-1}$ (Phthalimido C=O) 1770 cm$^{-1}$ (β-Lactam C=O) 1720 cm$^{-1}$ (Ester C=O)

Similarly, the analog 47 (X=N) was prepared, as well as the β-methyl derivatives 47a (X=N) and (X=CH).

EXAMPLE 58

(±)Potassium-(1R,5R,6S)-2-Acetoxymethyl-6-(N-phthalimido)-1-Methyl-Carbapen-2-em-3-Carboxylate 21, (X=OAc)

To a stirred solution of (±)allyl-(1R,5R,6S)-2-Acetoxymethyl-6-(N-Phthalimido)-1-methylcarbapen-2-em-3-carboxylate, 20 (X=OAc) (26 mG, 0.0613 mM) in 1:1 anhydrous mixture of methylene chloride:ethyl acetate (2 mL) in a centrifuge tube at room temperature under nitrogen were added triphenylphosphine (1.6 mG, 0.0026 mM), and potassium 2-ethylhexanoate (123 µL of 0.5 molar solution, ethyl acetate). A yellow precipitate formed within 2 minutes. This reaction mixture was stirred for 30 minutes, diluted with 2 mL of anhydrous ether, and centrifuged. The supernatant was removed. The solid was shaken with 2 mL of anhydrous ethyl acetate, centrifuged and liquid decanted. This procedure was repeated with 1×2 mL of ethyl acetate, and 2×2 mL of ether. The solid was taken up in 0.5 mL of water and applied on 1000µ reverse phase silica gel plate and eluted using 1:9 ethanol:water as solvent. The U.V. active area was scraped, stirred with 5 mL of 40% aqueous acetonitrile and filtered. The filtrate was washed with 4×5 mL of hexane. The aqueous phase was concentrated in vacuo at room temperature and freeze dried to give 10 mG of (±)potassium-(1R,5R,6S)-2-acetoxymethyl-6-(N-phthalimido)-1-methylcarbapen-2-em-3-carboxylate, 21, (X=OAc) as white foam.

NMR(D$_2$O): 1.24(d, J=7 Hz, CH$_3$) 1.18(s, acetate CH$_3$) 3.32–3.48(m, CHCH$_3$) 4.18–4.27(dd, J=5.5 & 8 Hz, H5) 5.0–5.39(dd, J=12 & 5.5 Hz, CH$_2$OAc) 5.97(d, J=5.5 Hz, H6) 7.92–8.04(phthalimido H's)

UV: λmax$^{H2O}$ 300 & 268 nm.

Similarly, the β-methyl isomer 21a (X=OAc) was also prepared, the phenyl and pyridyl derivatives 48, 48a (X=CH, N) are also similarly prepared.

EXAMPLE 59

1-(Chloromethylene)-Hexahydro-1H-Azepinium Chloride, 31

Ethyl formate (22.2 G, 0.3M) was added dropwise under nitrogen to hexahydro-1H-azepine (19.8 G, 0.2M) in such a way that a gentle reflux is maintained during the addition. The reaction mixture was then allowed to stir overnight. The volatile materials were evaporated at room temperature and ~20 mm. The residue was distilled in vacuo to give 1-(Formyl)-Hexahydro-1H-Azepine (bp. 56°–8°/3–4 mm; 84%).

To a solution of this distillate (1.27 G, 10 mM) in 20 mL of anhydrous chloroform at 0° under nitrogen was added oxalylchloride (873 µL, 10 mM). The mixture was stirred for 8 hours at room temperature. The solvent was removed in vacuo at <25° to give 1-(chloromethylene)-hexahydro-1H-azepinium chloride 31 (quantitative yield) as extremely hygroscopic solid. This crude product was stored in the freezer for extended periods of time without spoilage and used as the imminium chloride.

EXAMPLE 60

(±)-3s-[[(Hexahydro-1H-Azepin-1-yl)Methylene]Amino]-4R-[(1s)-4-(2,2-Dimethyl-1,3-Dioxolanyl)Ethyl]azetidin-2-one, 32

To a solution of (±)-3S-amino-4R[(1S)-4-(2,2-dimethyl-1,3-dioxolanyl]ethyl]azetidin-2-one, 23, (483 mG, 2.25 mM) in 5 mL of anhydrous methylene chloride at 0° under nitrogen were added triethylamine (840µ, 6 mM) followed by 1-(chloromethylene)-hexahydro-1H-azepinium chloride (546 mG, 3 mM). The reaction mixture was stirred under nitrogen at 0° for 1 hour, diluted with 35 mL of ethyl acetate, and washed with 2×15 mL of 10% sodium bicarbonate solution. The organic phase was dried over anhydrous magnesium sulfate. Solvent was removed to give an oil, which was chromatographed on silica gel using ethyl acetate as solvent to give (±)-3S-[[(hexahydro-1H-azepin-1-yl)methylene]amino]-4R[(1S)-4-(2,2-dimethyl-1,3-dioxolanyl]ethyl]azetidin-2-one 32 (520 mG, 71%) as light brown solid mixture of diastereomers.

NMR(CDCl$_3$): 0.86(d, J=7 Hz, CH$_3$) 1.34 & 1.40(2 singlets, acetonide CH$_3$'s) 2.05–2.26(m, CHCH$_3$) 3.60–3.68(dd, J=5 & 10 Hz, H4) 4.60–4.68(dd, J=5 & 2 Hz, H3) 7.50(s, N=CH)

IR(Thin Film): 1780 cm$^{-1}$ (β-Lactam C=O) 1665 cm$^{-1}$ (N-C=N)

Similarly, the β-methyl isomer 32a was prepared.

EXAMPLE 61

(±)-1-[[(Allyloxy)Carbonyl]Hydroxymethyl]-3S-[[(Hexahydro-1H-Azepin-1-yl)Methylene]Amino]-4R-[(1S)-4-(2,2-Dimethyl-1,3-Dioxolanyl)Ethyl]azetidin-2-one 33

To a stirred solution of (±)-3S-[[(hexahydro-1H-azepin-1-yl)methylene]amino]-4R-[(1S)-4-(2,2-dimethyl-1,3-dioxolanyl]ethyl]azetidin-2-one, 32, (500 mG, 1.55 mM) in 20 mL of anhydrous methylene chloride were added 396 mG (3 mM) of allyl glyoxalate monohydrate, 50 µL (0.35 mM) of triethylamine, and 10 G of anhydrous magnesium sulfate. This mixture was stirred under nitrogen for 5 hours and was filtered and washed with 3×10 mL of ethyl acetate. The filtrate was concentrated to give an oil, which was chromatographed on silica gel using ethylacetate as solvent to give 348 mG (51%) of (±)-1-[[(allyloxy)carbonyl]hydroxymethyl]-3S-[[(hexahydro-1H-azepin-1-yl)methylene]amino]-4R-[(1s)-4-(2,2-dimethyl-1,3-dioxolanyl]ethyl]azetidin-2-one, 33, as light brown oil.

NMR(CDCl₃): 0.91 & 0.97(2d, J=7 Hz, CH₃) 1.37 & 1.43(2 singlets, acetonide CH₃'s) 2.08-2.21(m, CHCH₃) 5.65(d, J=6 Hz, H3) 7.48 & 7.50(2 singlets, N=CH)

IR(Thin Film): 3380 cm⁻¹ (OH) 1760 cm⁻¹ (β-Lactam C=O) 1630 cm⁻¹ (N=CH-N)

Similarly, the β-methyl isomer 33a was also prepared.

EXAMPLE 62

(±)-1-[[(Allyloxy)Carbonyl](Triphenylphosphoranylidene)Methyl]-3S-[[(HexaHydro-1H-Azepin-1-yl)Methylene]Amino-4R-[(1S)-4-(2,2-Dimethyl-1,3-Dioxolanyl)Ethyl]Azetidin-2-one, 35

To a stirred solution of (±)-1-[[(allyloxy)carbonyl]-hydroxymethyl]-3S-[[(hexahydro-1H-azepin-1-yl)methylene]amino]-4S[(1S)-4-[(2,2-dimethyl-1,3-dioxolanylethylazetidin-2-one, 33, (180 mG, 0.413 mM) in 4 mL of anhydrous tetrahydrofuran under nitrogen were added 96 μL (0.825 mM) of 2,6-lutidine followed by 60 μL (0.825 mM) of thionyl chloride. A white precipitate formed immediately. After 40 minutes, the reaction mixture was diluted with 5 mL of cold (−40°) ethyl acetate and filtered. The filtrate was concentrated in vacuo at <25° to give the chloro derivative 34 as brown oil.

NMR(CDCl₃): 1.06(d, J=7 Hz, CH₃) 1.34, 1.38 & 1.43(acetonide CH₃'s) 5.82 & 6.03(2 singlets, CHCl) 7.8 & 7.85(2 singlets, N=CH)

IR(Thin Film): 1770 cm⁻¹ (β-Lactam C=O) 1690 cm⁻¹ (ester C=O) 1645 cm⁻¹ (N-C=N)

This residue was dissolved in 4 mL of anhydrous dimethylformamide containing 262 mG (1 mM) of triphenylphosphine and 116 μL (1 mM) of 2,6-lutidine was added. The mixture was heated overnight at 80° under nitrogen. Solvent was removed in vacuo at <25° C. The residue was shaken with 5 mL of ethyl acetate and 3 mL of water. Ethyl acetate layer was dried over anhydrous magnesium sulfate. Solvent removal gave the excess triphenylphosphine used in the reaction.

The aqueous phase was treated with 5 mL of 10% sodium bicarbonate solution and extracted with 3×2 mL of ethyl acetate. The combined ethyl acetate extracts were dried over anhydrous magnesium sulfate. Solvent removal gave 82 mG (23%) of (±)-1-[[(allyloxy)carbonyl](triphenylphosphoranylidene)methyl]-3S-[[(hexahydro-1H-azepin-1-yl)methylene]amino]-4R-[(1S)-4-(2,2-dimethyl-1,3-dioxolanyl)ethyl]azetidin-2-one 35 as thick brown oil.

NMR(CDCl₃): 0.75(d, J=7 Hz, CH₃) 1.32, 1.36, 1.38 & 1.40(singlets, acetonide CH₃'s)

IR(Thin Film): 1750 cm⁻¹ (β-Lactam C=O) 1600-1670 cm⁻¹ (ester C=O, N-C=N, and ylide)

Similarly, the β-methyl isomer 35a was prepared.

EXAMPLE 63

(±)-1-[[(Allyloxy)Carbonyl](Triphenylphosphoranylidene)methyl]-3S-[[(Hexahydro-1H-Azepin-1-yl)Methylene]-Amino]-4R-[(3S)-(1,2-dihydroxybutyl)-]Azetidin-2-one 36

(±)-1-[[(allyloxy)carbonyl](triphenylphosphoranylidene-methyl]-3S-[[(hexahydro-1H-azepin-1-yl)methylene]amino-4R-[(1S)-4-(2,2-dimethyl-1,3-dioxolanyl-)ethyl]azetidin-2-one, 35 (50 mG, 0.073 mM) was added to a stirred mixture of 500 μL of 9:1 trifluoroacetic acid-water at −50° C. The reaction mixture was stirred for 40 minutes as the temperature rose to 0° C. 10% sodium bicarbonate solution was added cautiously until no more effervescence was observed. It was then extracted with ethyl acetate (3×2 mL). The combined ethyl acetate extracts were dried over anhydrous magnesium sulfate and the solvent was removed in vacuo at room temperature to afford 34 mG (72%) of (±)-1-[[(allyloxy)carbonyl](triphenylphosphoranylidene)methyl]-3S-[[(hexahydro-1H-azepin-1-yl)methylene]amino]-4R-[(3S)-(1,2-dihydroxybutyl)]azetidin-2-one, 36 as a white foam.

Similarly, the β-methyl isomer 36a was prepared.

EXAMPLE 64

(±)Allyloxy-(1R,5R,6S)-6-[[)Hexahydro-1H-Azepin-1-yl]-1-Methylcarbapen-2-em-3-Carboxylate, 37

To a stirred solution of (±)-1-[[(allyloxy)carbonyl](-triphenylphosphoranylidene)methyl]-3S-[[(hexahydro-1H-azepin-1-yl)methylene]amino]-4R[(3S)-(1,2-dihydroxybutyl)azetidin-2-one, 36 (20 mG, 0.03 mM) in tetrahydrofuran was added periodic acid (20 mG, 0.09 mM). After stirring 5 minutes, a white precipitate formed. After 15 minute stirring, the reaction mixture was diluted with 5 mL of ethyl acetate and washed with 2×3 mL of 10% sodium bicarbonate solution, and 3 mL of saturated sodium chloride solution. The organic phase was dried over anhydrous magnesium sulfate. Solvent was removed in vacuo at room temperature to give 18 mG of (±)allyl-(1R,5R,6S)-6-[[(hexahydro-1H-azepin-1-yl)-1-methylcarbapen-2-em-3-carboxylate 37, contaminated with triphenylphosphine oxide, as oil.

NMR spectrum of this oil showed the presence of only the desired product along with triphenyloxide.

NMR(CDCl₃): 1.18(d, J=7 Hz, CH₃) 3.58-3.70(m, CHCH₃) 3.83-3.90(dd, J=5.5 & 8 Hz, H5) 4.90(d, J=5.5 Hz, H6) 6.47(d, J=2 Hz, H2)

IR(Thin Film): 1780 cm⁻¹(β-Lactam C=O) 1725 cm⁻¹(ester C=O) 1630 cm⁻¹(N=C-N)

Similarly, the β-methyl isomer 37a was also prepared.

EXAMPLE 65

(±)-(1R,5R,6S)-6-(Hexahydro-1-H-azepin-1-yl methyleneamino)-1-Methylcarbapen-2-em-3-carboxylic acid (38)

A mixture of 33.1 mg (0.1 mmol) of (±)-allyl-(1R,5R,6S)-6-(hexahydro-1H-azepin-1-yl methyleneamino)-1-methyl carbapen-2-em-3-carboxylate (37), 15.7 mg (0.06 mmol) triphenylphosphine, 23.1 mg (0.02 mmol) tetrakistriphenylphosphine palladium (O), and 15.8 mg (0.11 mmol) 2-ethylhexanoic acid in 2 mL methylene chloride-ethylacetate (1:1) and 2 mL 0.1M pH7 MOPS buffer is vigorously stirred in the cold for 0.5 hour. The organic phase is decanted and the aqueous phase washed first with ethylacetate and then with ether. Lyophilization of the aqueous solution provides the title compound 38.

EXAMPLE 66

(±)-1-(4-Methoxyphenyl)-3S-azido-4R-[(2S)-(1-Phenyl-1-Hydroxy)Propyl]azetidin-2-one, 39 (X=CH)

To a stirred solution of (±)-1-(4-methoxyphenyl)-3S-azido-(4R)-[(1S)-carboxaldehydoethyl]azetidin-2-one, 6, (1.37 G, 5 mM) in anhydrous tetrahydrofuran (20 mL) at −78° under nitrogen was added freshly prepared phenyl magnesium bromide (20 mL of 0.5M solution in tetrahydrofuran, 10 mM). After 30 minute stirring at −78°, the reaction mixture was quenched with 10 mL of saturated ammonium chloride solution, diluted with 20 mL of ethyl acetate. The organic phase was separated and washed with 20 mL of saturated sodium chloride solution, dried over anhydrous magnesium sulfate. Solvent removal gave yellow oil which was chromatographed on silica gel using 1:1 ether: petroleum ether as solvent to give (±)-1-(4'-methoxyphenyl)-3S-azido-4R-[(2S)-(1-phenyl-1-hydroxy)-propyl]azetidin-2-one, 39 (X=CH) as thick oil (89%).

NMR(CDCl$_3$): 0.79 & 0.97(2d, J=7 Hz, CH$_3$) 2.64–2.79(m, CHCH$_3$) 3.80(s, OCH$_3$) 5.02(d, J=5.5 Hz, H3) 6.86–7.42(aromatic H's)

Similarly, the β-methyl isomer 39a was also prepared.

What is claimed is:

1. A compound of the structural formula:

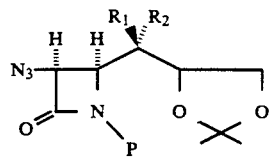

wherein R$_1$/R$_2$ is H/CH$_3$ or CH$_3$/H and P is hydrogen or a nitrogen-protecting group removable by acid or basic hydrolysis, catalytic hydrogenation, or oxidative cleavage.

2. A compound of the formula:

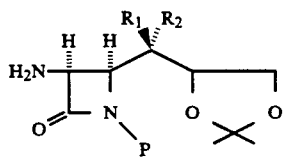

wherein R$_1$/R$_2$ is H/CH$_3$ or CH$_3$/H and P is hydrogen or a nitrogen-protecting group removable by acid or basic hydrolysis, catalytic hydrogenation, or oxidative cleavage.

* * * * *